(12) United States Patent
Hiemstra et al.

(10) Patent No.: US 12,193,839 B2
(45) Date of Patent: Jan. 14, 2025

(54) WEARABLE ELECTRONIC DEVICE WITH GLASS SHELL

(71) Applicant: Apple Inc., Cupertino, CA (US)

(72) Inventors: Daniel J. Hiemstra, San Jose, CA (US); Erik G. de Jong, San Francisco, CA (US); Sameer Pandya, Sunnyvale, CA (US)

(73) Assignee: APPLE INC., Cupertino, CA (US)

( * ) Notice: Subject to any disclaimer, the term of this patent is extended or adjusted under 35 U.S.C. 154(b) by 565 days.

(21) Appl. No.: 17/315,141

(22) Filed: May 7, 2021

(65) Prior Publication Data
US 2021/0353226 A1    Nov. 18, 2021

Related U.S. Application Data

(60) Provisional application No. 63/023,961, filed on May 13, 2020.

(51) Int. Cl.
*A61B 5/00* (2006.01)
*A61B 5/024* (2006.01)
(Continued)

(52) U.S. Cl.
CPC .......... *A61B 5/681* (2013.01); *A61B 5/02427* (2013.01); *A61B 5/14552* (2013.01);
(Continued)

(58) Field of Classification Search
CPC . A61B 5/681; A61B 5/02427; A61B 5/14552; A61B 5/256; A61B 5/282;
(Continued)

(56) References Cited

U.S. PATENT DOCUMENTS

| 4,106,839 | A | 8/1978 | Cooper |
| 4,256,412 | A | 3/1981 | Tybus et al. |

(Continued)

FOREIGN PATENT DOCUMENTS

| CN | 101087500 | 12/2007 |
| CN | 101350849 | 1/2009 |

(Continued)

OTHER PUBLICATIONS

Author Unknown, "Improved Touchscreen Products," Research Disclosure, Kenneth Mason Publications, Hampshire, UK, GB, vol. 428, No. 53, Dec. 1, 1999.

(Continued)

*Primary Examiner* — Eric F Winakur
*Assistant Examiner* — Abid A Mustansir
(74) *Attorney, Agent, or Firm* — Brownstein Hyatt Farber Schreck, LLP

(57) ABSTRACT

A wearable electronic device may include a display and a housing. The housing may include a chassis defining a first portion of a rear exterior surface of the wearable electronic device, a first portion of a side exterior surface of the wearable electronic device, and an internal wall. The housing may also include a glass shell defining a front wall positioned over the display and defining a front exterior surface of the wearable electronic device and a side wall extending from the front wall and overlapping the internal wall, the side wall defining a second portion of the side exterior surface of the wearable electronic device. The wearable electronic device may also include a touch sensing system within the housing and configured to detect a touch input applied to the front exterior surface of the wearable electronic device.

20 Claims, 19 Drawing Sheets

(51) Int. Cl.
    *A61B 5/1455*     (2006.01)
    *A61B 5/256*     (2021.01)
    *A61B 5/282*     (2021.01)
    *A61B 5/339*     (2021.01)
    *G04G 17/08*     (2006.01)
    *G06F 1/16*     (2006.01)
    *G06F 1/18*     (2006.01)
    *G06F 3/044*     (2006.01)

(52) U.S. Cl.
    CPC .............. *A61B 5/256* (2021.01); *A61B 5/282* (2021.01); *A61B 5/339* (2021.01); *A61B 5/7435* (2013.01); *G04G 17/08* (2013.01); *G06F 1/163* (2013.01); *G06F 1/181* (2013.01); *G06F 3/044* (2013.01)

(58) Field of Classification Search
    CPC ... A61B 5/339; A61B 5/7435; A61B 5/02416; G04G 17/08; G04G 21/025; G04G 21/08; G06F 1/163; G06F 1/181; G06F 3/044
    See application file for complete search history.

(56) References Cited

U.S. PATENT DOCUMENTS

| | | |
|---|---|---|
| 4,855,174 A | 8/1989 | Kamamoto et al. |
| 4,989,622 A | 2/1991 | Kozuka et al. |
| 5,055,347 A | 10/1991 | Bacon, Jr. |
| 5,512,374 A | 4/1996 | Wallace et al. |
| 6,061,104 A | 5/2000 | Evanicky et al. |
| 6,093,887 A | 7/2000 | Ponto et al. |
| 6,189,938 B1 | 2/2001 | Nakadaira et al. |
| 6,278,873 B1 | 8/2001 | Itakura et al. |
| 6,288,330 B1 | 9/2001 | Chen |
| 6,359,768 B1 | 3/2002 | Eversley et al. |
| 6,392,873 B1 | 5/2002 | Honda |
| 6,424,338 B1 | 7/2002 | Anderson et al. |
| 6,442,826 B1 | 9/2002 | Staudt et al. |
| 6,473,069 B1 | 10/2002 | Gerpheide |
| 6,483,024 B1 | 11/2002 | Smithson et al. |
| 6,589,891 B1 | 7/2003 | Rast |
| 6,654,256 B2 | 11/2003 | Gough |
| 6,671,160 B2 | 12/2003 | Hayden |
| 6,940,731 B2 | 9/2005 | Davis et al. |
| 6,996,425 B2 | 2/2006 | Watanabe |
| 7,048,242 B2 | 5/2006 | Oddsen, Jr. |
| 7,436,653 B2 | 10/2008 | Yang et al. |
| 7,491,900 B1 | 2/2009 | Peets et al. |
| 7,586,753 B2 | 9/2009 | Lu |
| 7,604,377 B2 | 10/2009 | Yu et al. |
| 7,755,913 B2 | 7/2010 | He |
| 7,829,812 B2 | 11/2010 | Tolbert et al. |
| 7,920,904 B2 | 4/2011 | Kim et al. |
| 7,986,525 B2 | 7/2011 | Wang |
| 8,066,233 B2 | 11/2011 | Fujikawa et al. |
| 8,092,897 B2 | 1/2012 | Honma et al. |
| 8,101,859 B2 | 1/2012 | Zadesky |
| 8,164,898 B2 | 4/2012 | Lin et al. |
| D660,193 S | 5/2012 | Neuner |
| 8,195,244 B2 | 6/2012 | Smoyer et al. |
| 8,199,488 B2 | 6/2012 | Zou et al. |
| 8,358,513 B2 | 1/2013 | Kim et al. |
| 8,396,521 B2 | 3/2013 | Horimoto et al. |
| 8,456,847 B2 | 6/2013 | Hwang et al. |
| 8,509,863 B2 | 8/2013 | Vedurmudi et al. |
| 8,553,907 B2 | 10/2013 | Thomason et al. |
| 8,558,977 B2 | 10/2013 | Gettemy et al. |
| 8,587,935 B2 | 11/2013 | Lee |
| 8,654,524 B2 | 2/2014 | Pance et al. |
| 8,665,236 B2 | 3/2014 | Myers |
| 8,675,359 B2 | 3/2014 | Chen |
| 8,681,115 B2 | 3/2014 | Kurita |
| 8,744,529 B2 | 6/2014 | Freund et al. |
| 8,773,848 B2 | 7/2014 | Russell-Clarke et al. |
| 8,824,140 B2 | 9/2014 | Prest et al. |
| 8,974,924 B2 | 3/2015 | Weber et al. |
| 8,975,540 B2 | 3/2015 | Mareno et al. |
| 9,007,748 B2 | 4/2015 | Jarvis |
| 9,086,748 B2 | 7/2015 | Nam et al. |
| 9,124,676 B2 | 9/2015 | Allore et al. |
| 9,135,944 B2 | 9/2015 | Jenks |
| 9,162,519 B2 | 10/2015 | Suehiro et al. |
| 9,173,306 B2 | 10/2015 | Lim et al. |
| 9,192,072 B2 | 11/2015 | Shin et al. |
| 9,203,463 B2 | 12/2015 | Asrani et al. |
| 9,218,116 B2 | 12/2015 | Benko et al. |
| 9,250,659 B2 | 2/2016 | Tsai et al. |
| 9,390,869 B2 | 7/2016 | Lee et al. |
| 9,429,997 B2 | 8/2016 | Myers et al. |
| 9,448,631 B2 | 9/2016 | Winter et al. |
| 9,489,054 B1 | 11/2016 | Sumsion et al. |
| 9,532,723 B2 | 1/2017 | Kim et al. |
| 9,621,218 B1 | 4/2017 | Glickman et al. |
| 9,642,241 B2 | 5/2017 | Huitema et al. |
| 9,654,164 B2 | 5/2017 | Irci et al. |
| 9,693,473 B2 | 6/2017 | Hibino et al. |
| 9,740,237 B2 | 8/2017 | Moore et al. |
| 9,804,635 B2 | 10/2017 | Kim et al. |
| 9,826,649 B2 | 11/2017 | Narajowski et al. |
| 9,898,903 B2 | 2/2018 | Khoshkava et al. |
| 9,939,784 B1 | 4/2018 | Berardinelli et al. |
| 9,955,603 B2 | 4/2018 | Kiple et al. |
| 10,013,075 B2 | 7/2018 | Shipman |
| 10,042,442 B2 | 8/2018 | Kwak |
| 10,110,267 B2 | 10/2018 | Kim et al. |
| 10,321,590 B2 | 6/2019 | Cater et al. |
| 10,424,765 B2 | 9/2019 | Hwang et al. |
| 10,468,753 B2 | 11/2019 | Kim et al. |
| 10,656,714 B2 | 5/2020 | Ligtenberg et al. |
| 10,705,570 B2 | 7/2020 | Kuna et al. |
| 10,871,828 B2 | 12/2020 | Ligtenberg et al. |
| 10,983,570 B1 | 4/2021 | Files et al. |
| 11,379,010 B2 | 7/2022 | Kuna et al. |
| 2002/0006687 A1 | 1/2002 | Lam |
| 2002/0072335 A1 | 6/2002 | Watanabe |
| 2002/0130981 A1 | 9/2002 | Ma et al. |
| 2004/0190239 A1 | 9/2004 | Weng |
| 2005/0140565 A1 | 6/2005 | Krombach |
| 2006/0203124 A1 | 9/2006 | Park et al. |
| 2007/0195495 A1 | 8/2007 | Kim et al. |
| 2007/0229702 A1 | 10/2007 | Shirono et al. |
| 2007/0287512 A1 | 12/2007 | Kilpi et al. |
| 2008/0018475 A1 | 1/2008 | Breed et al. |
| 2008/0084384 A1 | 4/2008 | Gregorio et al. |
| 2008/0174037 A1 | 7/2008 | Chen |
| 2008/0309640 A1 | 12/2008 | Hong et al. |
| 2009/0003141 A1 | 1/2009 | Ozawa et al. |
| 2009/0041984 A1 | 2/2009 | Mayers et al. |
| 2009/0219156 A1 | 9/2009 | August et al. |
| 2009/0278688 A1 | 11/2009 | Tuttle |
| 2009/0295943 A1 | 12/2009 | Kim et al. |
| 2009/0298547 A1 | 12/2009 | Kim et al. |
| 2010/0061044 A1 | 3/2010 | Zou et al. |
| 2010/0091442 A1 | 4/2010 | Theobald et al. |
| 2010/0105452 A1 | 4/2010 | Shin et al. |
| 2010/0137043 A1 | 6/2010 | Horimoto et al. |
| 2010/0151925 A1 | 6/2010 | Vedurmudi et al. |
| 2010/0157515 A1 | 6/2010 | Tseng et al. |
| 2010/0265182 A1 | 10/2010 | Ball et al. |
| 2010/0302016 A1 | 12/2010 | Zaborowski et al. |
| 2010/0308998 A1 | 12/2010 | Hesch, Jr. et al. |
| 2010/0315399 A1 | 12/2010 | Davis et al. |
| 2011/0038114 A1 | 2/2011 | Pance et al. |
| 2011/0047459 A1 | 2/2011 | Van Der Westhuizen |
| 2011/0065479 A1 | 3/2011 | Nader |
| 2011/0091051 A1 | 4/2011 | Thomason et al. |
| 2011/0095994 A1 | 4/2011 | Birnbaum |
| 2011/0205169 A1 | 8/2011 | Yasutake et al. |
| 2011/0292579 A1 | 12/2011 | Koga |
| 2012/0009983 A1 | 1/2012 | Mow et al. |
| 2012/0069517 A1 | 3/2012 | Prest et al. |
| 2012/0088072 A1 | 4/2012 | Pawloski et al. |
| 2012/0094594 A1 | 4/2012 | Rofougaran et al. |

(56) References Cited

U.S. PATENT DOCUMENTS

| | | |
|---|---|---|
| 2012/0097412 A1 | 4/2012 | Wennemer et al. |
| 2012/0175165 A1 | 7/2012 | Merz et al. |
| 2012/0212424 A1 | 8/2012 | Sharma et al. |
| 2012/0236477 A1 | 9/2012 | Weber |
| 2012/0268412 A1 | 10/2012 | Cruz-Hernandez et al. |
| 2012/0274575 A1 | 11/2012 | Solomon et al. |
| 2012/0327008 A1 | 12/2012 | Kurita |
| 2013/0051000 A1 | 2/2013 | Yu et al. |
| 2013/0076649 A1 | 3/2013 | Myers et al. |
| 2013/0273295 A1 | 10/2013 | Kenney et al. |
| 2013/0308282 A1 | 11/2013 | Shin et al. |
| 2014/0015773 A1 | 1/2014 | Loeffler |
| 2014/0031093 A1 | 1/2014 | Song et al. |
| 2014/0139450 A1 | 5/2014 | Levesque et al. |
| 2014/0253487 A1* | 9/2014 | Bezinge ............... G04G 21/08 345/173 |
| 2014/0288438 A1 | 9/2014 | Venkatraman et al. |
| 2014/0298478 A1 | 10/2014 | Kim et al. |
| 2014/0311767 A1 | 10/2014 | Merz et al. |
| 2014/0320344 A1 | 10/2014 | Sanderovich et al. |
| 2014/0320435 A1* | 10/2014 | Modarres ............. G06F 1/1652 345/173 |
| 2014/0347799 A1 | 11/2014 | Ono et al. |
| 2014/0368455 A1 | 12/2014 | Croisonnier et al. |
| 2015/0001104 A1 | 1/2015 | Kim et al. |
| 2015/0062419 A1 | 3/2015 | Hooton et al. |
| 2015/0090571 A1 | 4/2015 | Leong et al. |
| 2015/0109223 A1 | 4/2015 | Kessler et al. |
| 2015/0124401 A1 | 5/2015 | Prest et al. |
| 2015/0171916 A1 | 6/2015 | Asrani et al. |
| 2015/0183185 A1 | 7/2015 | Chang |
| 2015/0185946 A1 | 7/2015 | Fourie |
| 2015/0255853 A1 | 9/2015 | Kwong et al. |
| 2015/0364820 A1 | 12/2015 | Dong et al. |
| 2016/0029899 A1 | 2/2016 | Kim et al. |
| 2016/0034042 A1 | 2/2016 | Joo et al. |
| 2016/0055729 A1 | 2/2016 | Maddox et al. |
| 2016/0064820 A1 | 3/2016 | Kim et al. |
| 2016/0098016 A1 | 4/2016 | Ely et al. |
| 2016/0098107 A1 | 4/2016 | Morrell et al. |
| 2016/0103544 A1 | 4/2016 | Filiz et al. |
| 2016/0147257 A1 | 5/2016 | Yamazaki |
| 2016/0254587 A1 | 9/2016 | Jung et al. |
| 2016/0255944 A1 | 9/2016 | Baranski et al. |
| 2016/0270247 A1 | 9/2016 | Jones et al. |
| 2016/0308563 A1 | 10/2016 | Ouyang et al. |
| 2016/0316574 A1 | 10/2016 | Chang et al. |
| 2016/0327980 A1 | 11/2016 | Farahani et al. |
| 2016/0327986 A1 | 11/2016 | Farahani et al. |
| 2017/0010771 A1 | 1/2017 | Bernstein et al. |
| 2017/0038793 A1 | 2/2017 | Kallman |
| 2017/0048495 A1 | 2/2017 | Scalisi et al. |
| 2017/0060201 A1 | 3/2017 | Prather et al. |
| 2017/0094804 A1 | 3/2017 | Brodsky et al. |
| 2017/0104261 A1 | 4/2017 | Wong et al. |
| 2017/0230073 A1 | 8/2017 | Youn et al. |
| 2017/0264008 A1 | 9/2017 | Ying et al. |
| 2017/0264722 A1 | 9/2017 | Zhong |
| 2017/0303048 A1 | 10/2017 | Hooton et al. |
| 2018/0020208 A1 | 1/2018 | Woo et al. |
| 2018/0026341 A1 | 1/2018 | Mow et al. |
| 2018/0026353 A1 | 1/2018 | Tseng et al. |
| 2018/0077328 A1 | 3/2018 | Park et al. |
| 2018/0090847 A1 | 3/2018 | Romano et al. |
| 2018/0198212 A1 | 7/2018 | Rodriguez |
| 2018/0210515 A1 | 7/2018 | Lyles et al. |
| 2018/0213660 A1 | 7/2018 | Prest et al. |
| 2018/0217669 A1 | 8/2018 | Ligtenberg et al. |
| 2018/0284845 A1 | 10/2018 | Honma et al. |
| 2019/0020365 A1 | 1/2019 | Ouyang et al. |
| 2019/0083715 A1 | 3/2019 | Redmond et al. |
| 2019/0090806 A1* | 3/2019 | Clavelle ............... A61B 5/681 |
| 2019/0101960 A1 | 4/2019 | Silvanto et al. |
| 2019/0103682 A1 | 4/2019 | Thai et al. |
| 2019/0128669 A1 | 5/2019 | Nobayashi et al. |
| 2019/0312334 A1 | 10/2019 | Shin et al. |
| 2019/0361543 A1 | 11/2019 | Zhang |
| 2019/0377385 A1 | 12/2019 | Bushnell |
| 2020/0057525 A1 | 2/2020 | Prest et al. |
| 2020/0058992 A1 | 2/2020 | Wu et al. |
| 2020/0073445 A1 | 3/2020 | Kuna et al. |
| 2020/0076056 A1 | 3/2020 | Froese et al. |
| 2020/0076057 A1 | 3/2020 | Leutheuser et al. |
| 2020/0076058 A1 | 3/2020 | Zhang et al. |
| 2020/0278747 A1 | 9/2020 | Ligtenberg et al. |
| 2020/0314567 A1 | 10/2020 | Shriner et al. |
| 2020/0328499 A1 | 10/2020 | O'Driscoll et al. |
| 2020/0409023 A1 | 12/2020 | Kazuo et al. |
| 2021/0149458 A1 | 5/2021 | Silvanto et al. |
| 2021/0167487 A1 | 6/2021 | Vanna et al. |
| 2021/0234403 A1 | 7/2021 | Ku et al. |
| 2022/0004837 A1 | 1/2022 | Perkins et al. |
| 2022/0006176 A1 | 1/2022 | Froese et al. |
| 2022/0057885 A1 | 2/2022 | Prest et al. |
| 2022/0059928 A1 | 2/2022 | Leutheuser et al. |
| 2022/0317740 A1 | 10/2022 | Kuna et al. |
| 2022/0326777 A1 | 10/2022 | Ligtenberg et al. |
| 2023/0161390 A1 | 6/2023 | Silvanto et al. |
| 2023/0333600 A1 | 10/2023 | Kuna et al. |

FOREIGN PATENT DOCUMENTS

| | | |
|---|---|---|
| CN | 101753655 | 6/2010 |
| CN | 102159045 | 8/2011 |
| CN | 102405453 | 4/2012 |
| CN | 202281978 | 6/2012 |
| CN | 202735925 | 2/2013 |
| CN | 102984904 | 3/2013 |
| CN | 103168280 | 6/2013 |
| CN | 203054674 | 7/2013 |
| CN | 103327758 | 9/2013 |
| CN | 103390793 | 11/2013 |
| CN | 203416294 | 1/2014 |
| CN | 103681061 | 3/2014 |
| CN | 103777765 | 5/2014 |
| CN | 104427048 | 3/2015 |
| CN | 104582379 | 4/2015 |
| CN | 104742308 | 7/2015 |
| CN | 105228966 | 1/2016 |
| CN | 105892568 | 8/2016 |
| CN | 107221506 | 9/2017 |
| CN | 107275751 | 10/2017 |
| CN | 107317121 | 11/2017 |
| CN | 107534223 | 1/2018 |
| CN | 107735903 | 2/2018 |
| CN | 207216299 | 4/2018 |
| CN | 108400425 | 8/2018 |
| CN | 108594622 | 9/2018 |
| CN | 108594623 | 9/2018 |
| CN | 208385608 | 1/2019 |
| CN | 109546295 | 3/2019 |
| CN | 109980332 | 7/2019 |
| CN | 112532263 | 3/2021 |
| CN | 112799294 | 5/2021 |
| EP | 2565742 | 3/2013 |
| EP | 2843501 | 3/2015 |
| EP | 2993730 | 3/2016 |
| EP | 3144768 | 3/2017 |
| EP | 3438786 | 2/2019 |
| GB | 2516439 | 1/2015 |
| GB | 2529885 | 3/2016 |
| JP | S58151619 | 9/1983 |
| JP | H61039144 | 2/1986 |
| JP | H05022023 | 1/1993 |
| JP | H09232849 | 9/1997 |
| JP | H10102265 | 4/1998 |
| JP | H63249697 | 10/1998 |
| JP | 2001216077 | 8/2001 |
| JP | 20023431 F | 11/2002 |
| JP | 2004272690 | 9/2004 |
| JP | 2006243812 | 9/2006 |
| JP | 2007072375 | 3/2007 |
| JP | 2011014149 | 1/2011 |
| JP | 2011159276 | 8/2011 |

(56) References Cited

FOREIGN PATENT DOCUMENTS

| | | |
|---|---|---|
| JP | 2011239139 | 11/2011 |
| JP | 2011248888 | 12/2011 |
| JP | 2011249126 | 12/2011 |
| JP | 2012/019526 | 1/2012 |
| JP | 2012027592 | 2/2012 |
| JP | 2012222553 | 11/2012 |
| JP | 2013508818 | 3/2013 |
| JP | 2014501070 | 1/2014 |
| JP | 2014078240 | 5/2014 |
| JP | 2014512879 | 5/2014 |
| JP | 2014186075 | 10/2014 |
| JP | 2015031952 | 2/2015 |
| JP | 2019537909 | 12/2019 |
| KR | 20110049416 | 5/2011 |
| KR | 20110076951 | 7/2011 |
| KR | 20130096048 | 8/2013 |
| KR | 20140017420 | 2/2014 |
| KR | 20150012312 | 2/2015 |
| KR | 20160019833 | 2/2016 |
| KR | 20160052275 | 5/2016 |
| KR | 20160134504 | 11/2016 |
| KR | 20180025126 | 3/2018 |
| KR | 20190118095 | 10/2019 |
| TW | 201129285 | 8/2011 |
| TW | 201532835 | 9/2015 |
| TW | 201701119 | 1/2017 |
| WO | WO00/14826 | 3/2000 |
| WO | WO2009/002605 | 12/2008 |
| WO | WO2009/033616 | 3/2009 |
| WO | WO2009/049331 | 4/2009 |
| WO | WO2009/129123 | 10/2009 |
| WO | WO2011/130849 | 10/2011 |
| WO | WO2012/006152 | 1/2012 |
| WO | WO2012/129247 | 9/2012 |
| WO | WO2014/037945 | 3/2014 |
| WO | WO2014/149172 | 9/2014 |
| WO | WO2014/182392 | 11/2014 |
| WO | WO2015/153701 | 10/2015 |
| WO | WO2016/039803 | 3/2016 |
| WO | WO2016/053901 | 4/2016 |
| WO | WO2016/168432 | 10/2016 |
| WO | WO2018/013573 | 1/2018 |
| WO | WO2018/090295 | 5/2018 |

OTHER PUBLICATIONS

Kim et al., "Ultrathin Cross-Linked Perfluoropolyether Film Coatings from Liquid $CO_2$ and Subsequent UV Curing," Chem. Matter, vol. 22, pp. 2411-2413, 2010.

Author Unknown, "Smart Watch—New Fashion Men/women Bluetooth Touch Screen Smart Watch Wrist Wrap Watch Phone," https://www.fargoshopping.co.ke/, 5 pages, Mar. 2016.

International Search Report and Written Opinion, PCT/US2021/031352, 10 pages, Aug. 5, 2021.

\* cited by examiner

WEARABLE ELECTRONIC DEVICE WITH GLASS SHELL

CROSS-REFERENCE TO RELATED APPLICATION(S)

This application is a nonprovisional patent application of and claims the benefit of U.S. Provisional Patent Application No. 63/023,961, filed May 13, 2020 and titled "Wearable Electronic Device with Glass Shell," the disclosure of which is hereby incorporated herein by reference in its entirety.

FIELD

The subject matter of this disclosure relates generally to electronic devices and, more particularly, to housing structures for handheld electronic devices.

BACKGROUND

Modern consumer electronic devices take many shapes and forms, and have numerous uses and functions. Devices such as mobile phones, tablet computers, and watches, for example, may include touch-sensitive displays, speakers, microphones, batteries, as well as sophisticated processors and other electronics. These and other subsystems may be integrated into compact, handheld and/or wearable products that provide myriad functions while being reliable and capable of withstanding daily use.

SUMMARY

A wearable electronic device may include a display, a housing that includes a chassis defining a first portion of a rear exterior surface of the wearable electronic device and a first portion of a side exterior surface of the wearable electronic device, a glass shell defining a front wall positioned over the display and defining a front exterior surface of the wearable electronic device, and a side wall extending from the front wall and defining a second portion of the side exterior surface of the wearable electronic device. The wearable electronic device may further include a touch sensing system within the housing and configured to detect a touch input applied to the front exterior surface of the wearable electronic device.

The chassis may further define an internal wall, a portion of the side wall may overlap the internal wall and define a concave interior surface, and the wearable electronic device may further include an adhesive bonding the concave interior surface to the internal wall. The adhesive may define an undercut region, and the concave interior surface of the glass shell may mechanically interlock with the undercut region of the adhesive to secure the glass shell to the chassis. The glass shell may be secured to the chassis at least in part via a chemical bond between the concave interior surface and the adhesive. The second portion of the side exterior surface of the wearable electronic device may extend more than half of a distance from the front exterior surface of the wearable electronic device to the rear exterior surface of the wearable electronic device.

The wearable electronic device may further include a compliant member within the housing and in contact with the internal wall and the side wall, the compliant member defining a seal between the internal wall and the side wall.

The front wall may further define a front interior surface of the wearable electronic device, the wearable electronic device may further include an opaque mask material on a portion of the concave interior surface and on a portion of the front interior surface, and the opaque mask material may define a border around an active area of the display. The display may define a first portion configured to display first graphical outputs through the front wall and a second portion configured to display second graphical outputs through the side wall.

A watch may include a display, a capacitive touch-sensing system, and a housing surrounding the display and the capacitive touch-sensing system. The housing may include a glass shell defining a front wall defining a front surface of the watch, a first pair of side walls having a first length and defining a first pair of side surfaces of the watch, and a second pair of side walls having a second length greater than the first length and defining a second pair of side surfaces of the watch. The housing may also include a chassis defining at least a portion of a rear surface of the watch and a watch band engagement feature. The watch may include a watch band coupled to the watch band engagement feature.

The chassis may be formed from metal and may define a rear wall defining the portion of the rear surface of the watch and a hole extending through the rear wall. The watch may further include a sensor cover positioned at least partially in the hole and defining an additional portion of the rear surface of the watch and a sensor system configured to detect a biological parameter of a user through the sensor cover. The display may be configured to display graphical outputs visible through the front wall and through at least one side wall of the second pair of side walls.

The chassis may define an internal wall, and a first portion of the internal wall may overlap a first portion of one of the side walls of the second pair of side walls. The watch may further include an adhesive positioned in a gap defined between the first portion of the internal wall and the first portion of the side wall of the second pair of side walls. The watch band engagement feature may include a slot formed in the chassis.

A wearable electronic device may include a housing that includes a chassis defining a rear wall defining a first portion of a rear exterior surface of the wearable electronic device and a hole extending through the rear wall. The housing may also include a glass shell defining a front wall defining a front surface of the wearable electronic device and four side walls extending from the front wall, each of the four side walls defining a portion of a respective side surface of the wearable electronic device. The wearable electronic device may further include a sensor cover covering the hole and defining a second portion of the rear exterior surface of the wearable electronic device, a display within the housing, and a biometric sensor system within the housing and configured to detect a biological parameter of a user.

The biometric sensor system may include an optical emitter configured to emit light through a first transparent portion of the sensor cover, and an optical sensor configured to detect, through a second transparent portion of the sensor cover, a portion of the light that is reflected by a portion of the user's body. The sensor cover may include a monolithic structure formed from a transparent material, a masked region defining an opaque region of the sensor cover, a first unmasked region defining the first transparent portion of the sensor cover, and a second unmasked region defining the second transparent portion of the sensor cover.

The wearable electronic device may further include an electrode coupled to the sensor cover and defining a third portion of the rear exterior surface of the wearable electronic device. The electrode may be a first electrode configured to measure a first voltage, the wearable electronic device may further include a second electrode along an exterior surface of the wearable electronic device and configured to measure a second voltage, and the wearable electronic device may be configured to determine an electrocardiogram using the first voltage and the second voltage. The second electrode may be positioned along one of the side walls of the four side walls.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The embodiments described herein are generally directed to electronic watches having housings that include glass shells that define multiple sides of the devices. Conventionally, glass has been used in such devices to provide a transparent window over a touchscreen on a front of the device. Described herein, however, are electronic devices with housings that use glass to define front surfaces as well as multiple side exterior surfaces of the housing. For example, a housing for an electronic watch, also referred to as a smartwatch, may include a glass shell that resembles a five-sided box that fits onto (and is coupled to) a chassis or frame member. The glass shell may have a front glass wall that defines a front surface of the watch, as well as multiple side walls, each extending away from the front wall and each respective side wall defining at least part of a respective side surface of the housing. This configuration allows a significant amount of mechanical overlap between the chassis and the glass shell, and thus may increase the strength of the mechanical coupling between the glass shell and the chassis. Further, by forming the side walls of the watch entirely or substantially entirely out of glass, additional functional and aesthetic benefits are realized. For example, displays may be positioned adjacent the side walls to display graphical outputs on (or through) the side walls. Sensors, such as touch sensors, biometric sensors, etc., may leverage the transparent and/or dielectric properties of the glass side walls to sense or detect inputs applied to the side walls.

The configuration of the side walls of the glass shell also result in the seams or joints between the glass structure and the chassis being positioned further towards the rear of the watch (as compared to conventional watch configurations), away from the user-facing surfaces. This may result in a less distracting, more attractive aesthetic appearance, as there may be fewer distracting seams or other discontinuities between housing components. The glass shell may also improve the water resistance of the watch, as the seams between housing components, where water or other liquids may accumulate, may be positioned further away from the source of the liquid (e.g., rain, sweat, splashes, etc., that may primarily or initially contact the front surface of a watch).

Figure 1A:
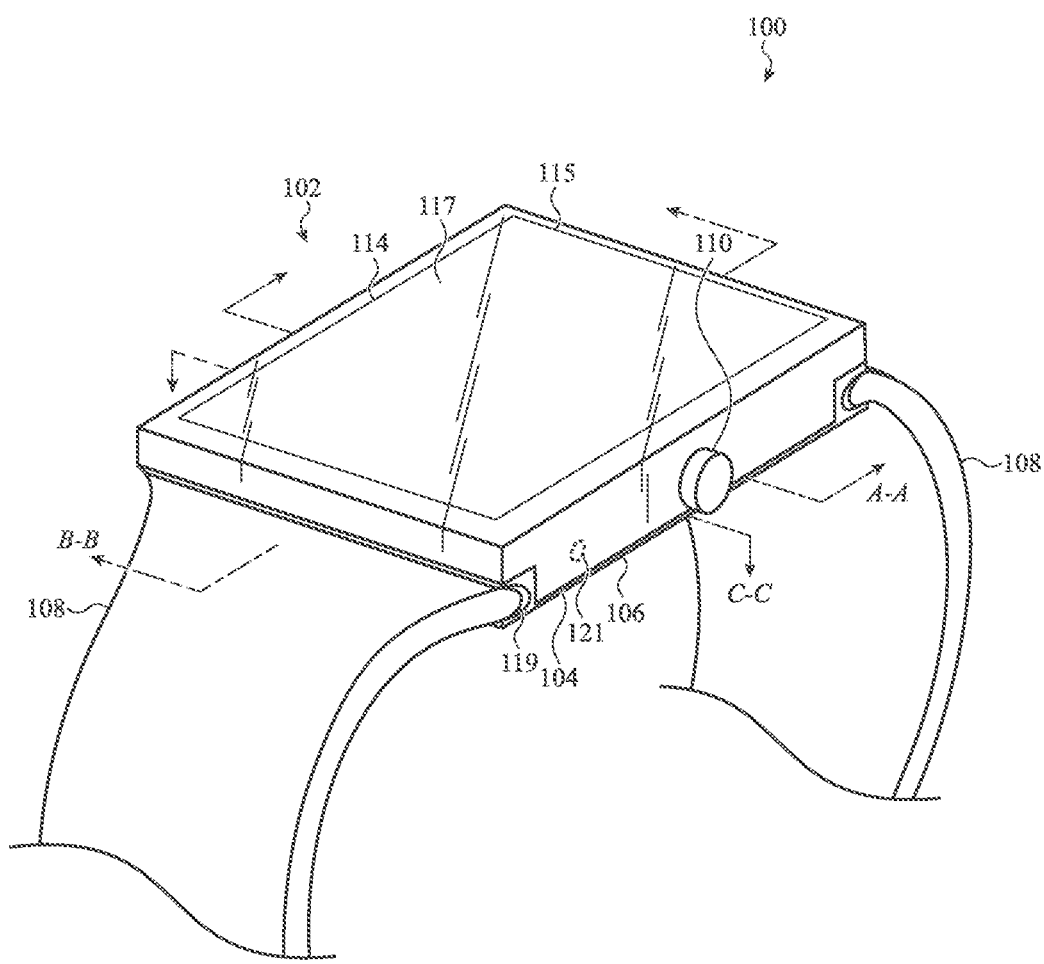
FIGS. 1A-1C depict an example electronic device.
Figure 1B:
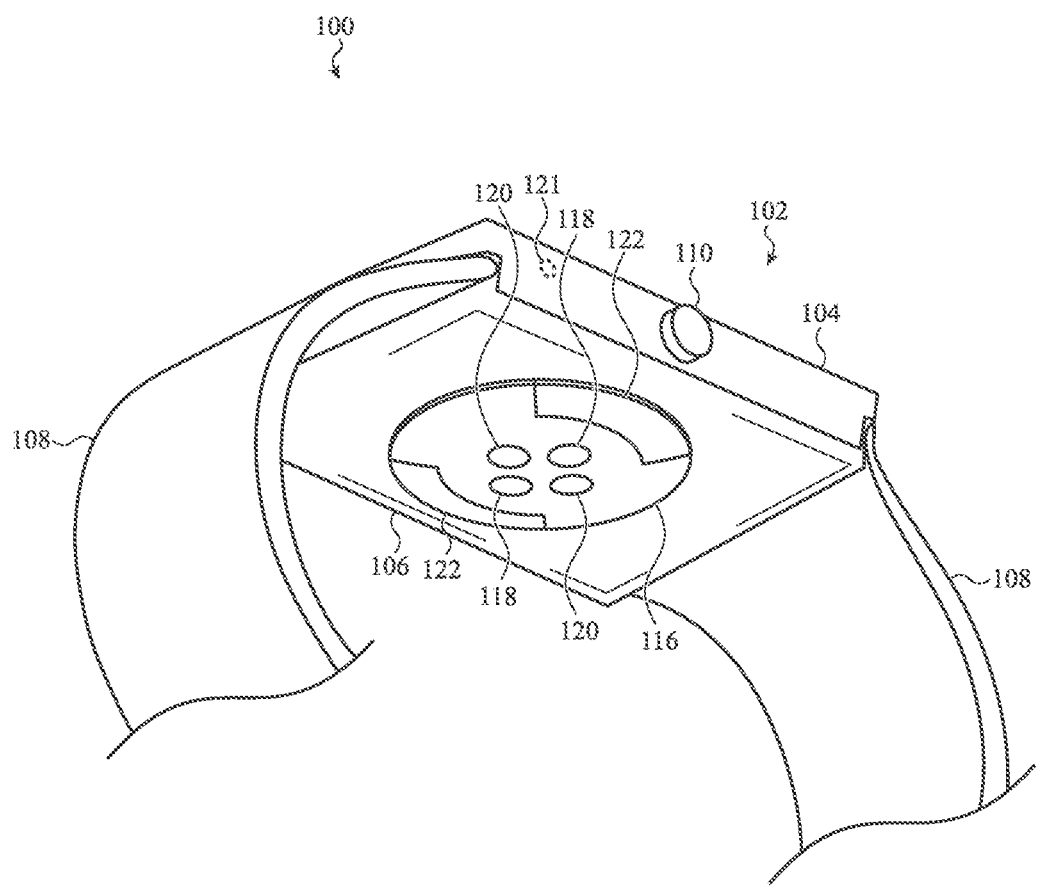

FIGS. 1A-1B depict an example wearable electronic device 100. While the instant figures illustrate the wearable electronic device 100 as an electronic watch, this is merely one example embodiment of an electronic device that uses the concepts discussed herein, and the concepts, structures, principles, and techniques described herein may apply equally or by analogy to other electronic devices, including mobile phones, tablet computers, fitness trackers, GPS devices, notebook computers, digital media players (e.g., mp3 players), or other handheld devices, wearable devices, and/or other electronic devices.

The wearable electronic device 100 (also referred to herein as a watch 100) includes a housing 102 and a band 108 coupled to the housing 102. The band 108 may be configured to attach the watch 100 to a user, such as to the user's arm or wrist.

The housing 102 may at least partially define an internal volume in which components of the watch 100 may be positioned. The housing 102 may also define one or more exterior surfaces of the electronic device, such as all or a portion of one or more side surfaces, a rear surface, a front surface, and the like. The housing 102 may have a generally rectangular shape, when viewed from the front. In such cases, the housing 102 may have four sides and/or side surfaces, and four corners. In some cases, the four sides include a first pair of equal-length sides, and a second pair of equal-length sides that are shorter than the first pair of equal-length sides. Other shapes are also contemplated, such as generally square shapes (where all of the sides are substantially the same length).

Figure 1C:
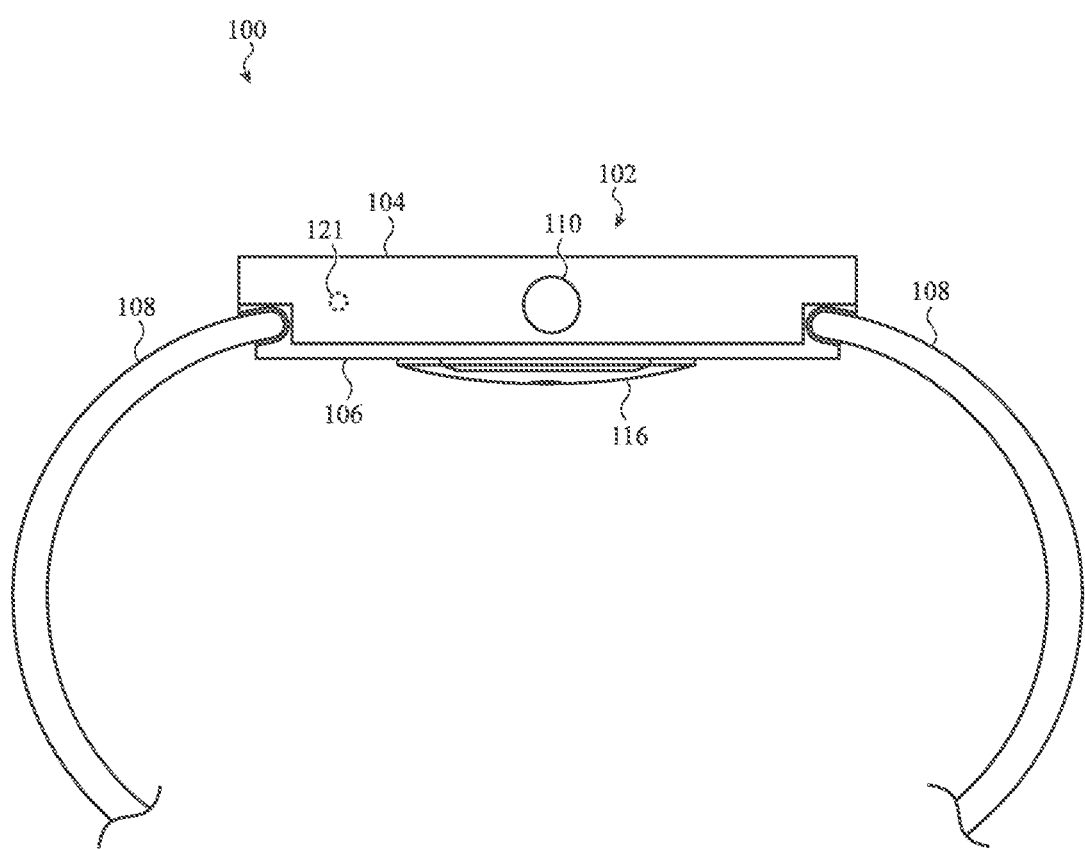

The housing 102 may include a shell 104 coupled to a chassis 106. The chassis 106 may be formed of metal (e.g., aluminum, steel, titanium, magnesium, a metal alloy, etc.), or another suitable material such as a polymer, a ceramic, glass, or the like. As described herein, the shell 104 may define multiple walls and multiple exterior surfaces of the housing 102. For example, the shell 104 may define a front wall that defines a front exterior surface of the watch 100, and multiple (e.g., four) respective side walls that each extend rearward from the front wall to define at least a portion of respective side exterior surfaces of the watch 100. The side walls of the shell 104 may define flat side surfaces, as shown in FIGS. 1A-1C, or they may be curved, rounded, semi-circular, or any other suitable shape. The transition between the side walls and the top or front wall of the shell 104 (e.g., where the side wall meets a front wall) may be sharp (e.g., defining a distinct apex or edge), curved, chamfered, rounded, or the like.

The front surface of the shell 104 may define all or substantially all of the front surface of the housing 102 (and thus the watch). In such cases, the shell 104 is continuous along the front surface, and does not have a hole or other allowance for a separate display cover. In other examples, the front of the shell 104 defines a hole, and a separate display cover is positioned in the hole and attached to the shell 104 or another structure of the device 100. In cases where the front surface of the shell 104 is continuous, the border of the display 114 shown in FIG. 1A does not correspond to a seam or opening in the shell 104, but instead represents the border of the display 114, a mask that defines a viewable area of the display (e.g., an output region 117), or the like. In cases where the shell 104 defines an opening in which a display cover is positioned, the border of the display 114 as shown in FIG. 1A may represent a seam between the display cover and the shell 104.

The shell 104 may also define one or more through holes to allow components such as speakers, microphones, barometric sensors, vents, or other components to have access to the external environment. For example, FIGS. 1A-1C illustrate an example location of a through hole 121. The through hole may be positioned in a side wall of the shell 104, as shown. Other through holes may be positioned elsewhere on the shell 104, such as through a different side wall or the front wall.

The shell 104 may be formed from glass, and may be referred to as a glass shell. Where the shell 104 is formed from glass, it may be formed from any suitable glass, and may be strengthened, tempered, or processed in any other suitable way to provide a target strength, toughness, scratch resistance, appearance, or other property. Example glass compositions may include, without limitation, soda lime glass, aluminosilicate glass, borosilicate glass, glass ceramic, or the like. The glass material may be chemically strengthened (e.g., via ion exchange baths or other techniques), annealed, tempered, or processed using other techniques. The shell 104 may also include one or more coatings, such as oleophobic coatings, anti-reflective coatings, anti-scratch coatings, or any other suitable coatings, films, layers, or the like.

The shell 104, or glass shell, may be formed using any suitable technique. For example, the shell 104 may be machined from a single block of glass. As another example, the shell 104 may be formed by slumping and/or molding a sheet of glass. As yet another example, the shell 104 may be formed by attaching multiple pieces of glass together. In the latter example, four glass side walls may be attached to a glass front wall, or two glass side walls may be attached to a glass structure that itself defines a front wall and two side walls. Glass pieces may be attached together using fusion bonding techniques (e.g., softening or melting portions of the glass members and joining them so that they fuse together), adhesives, or any other suitable technique.

In other cases, the shell 104 may be formed from materials other than glass, such as ceramics, glass ceramics, sapphire, polymers, composites, laminates, or the like. The material for the shell 104 may be optically transparent to facilitate the visibility of displays inside the device. The material for the shell 104 may also be a dielectric material or other material that facilitates the transmission and/or receipt of wireless signals into and/or out of the device. For example, the material may be selected so as to not significantly attenuate wireless signals to and/or from antennas inside the device.

The chassis 106 may define at least a portion of a rear exterior surface of the watch 100, and may also define a portion of one or more side exterior surfaces of the watch 100. The chassis 106 may also define band engagement features 119. The band engagement features 119 may facilitate the attachment of the watch band 108 to the housing 102. As shown, the band engagement features 119 include slots that receive end portions of the band 108, though other types of band engagement features 119 are also contemplated. For example, the band engagement features 119 may be lugs (e.g., protruding features with holes for accepting spring bars), holes (e.g., threaded holes), bars (e.g., about which bands may be wrapped), or other suitable band engagement features. While the housing 102 is largely defined by the shell 104, a non-glass chassis 106 may have a relatively greater strength and/or resistance to breaking than the shell 104. Accordingly, configuring the chassis 106 to include the band engagement features (or at least to define a load-bearing portion of the band engagement features) may result in a robust and secure band attachment while maintaining the functional and aesthetic benefits of the shell 104.

The shell 104 may cover (e.g., overlie) at least part of a display 114 that is positioned at least partially within the internal volume of the housing 102. The display 114 may define or correspond to an output region 117 in which graphical outputs are displayed. Graphical outputs may include graphical user interfaces, user interface elements (e.g., buttons, sliders, etc.), text, lists, photographs, videos, or the like. The display 114 may include a liquid crystal display (LCD), an organic light emitting diode display (OLED), or any other suitable components or display technologies. The display 114 may also include or be associated with touch and/or force sensing components, as described herein.

The shell 104 may include a mask along a mask region 115. The mask region 115 may form a border around and/or define the output region 117. The mask may be an opaque material (e.g., one or more layers of ink, dye, film, etc.) that is attached to an inner surface of the shell 104. The mask may visually occlude internal components of the watch 100. In some cases, the mask is configured to have an appearance (e.g., color, apparent texture, etc.) that is similar to the appearance of the display 114 when the display 114 is inactive. In this way, the border between the display 114 and the mask may be visually indistinguishable to the naked eye (at a certain distance, such as 1 foot, 2 feet, 3 feet, or the like).

The display 114 may include or be associated with touch sensors and/or force sensors that extend along the output region of the display and which may use any suitable sensing elements and/or sensing systems and/or techniques. Using touch sensors, the watch 100 may detect touch inputs applied to the shell 104, including detecting locations of touch inputs, motions of touch inputs (e.g., the speed, direction, or other parameters of a gesture applied to the shell 104), or the like. Using force sensors, the watch 100 may detect amounts or magnitudes of force associated with touch events applied to the shell 104. The touch and/or force sensors may detect various types of user inputs to control or modify the operation of the device, including taps, swipes, multi-finger inputs, single- or multi-finger touch gestures, presses, and the like. Further, as described herein, the touch and/or force sensors may detect motion of an object (e.g., a user's finger) as it is interacting with a crown 110 of the watch 100.

The watch 100 may also be configured to produce haptic (e.g., tactile) outputs that are detectable by a wearer or user of the watch 100. The watch 100 may produce haptic outputs in various ways. For example, the watch 100 may include a movable mass that moves (e.g., oscillates or vibrates translationally and/or rotationally, or otherwise moves to produce a tactile output), which may be detectable by a user when the user is wearing or otherwise contacting (e.g., touching) the watch 100. Haptic outputs may be produced in response to the watch 100 detecting an input or other user interaction, such as a touch input, a force input, a crown rotation, translation, or other interaction, a button press, or the like.

The watch 100 also includes a crown 110 (also referred to herein as a crown assembly) having a knob, external portion, or component(s) or feature(s) positioned along a side wall of the housing 102. At least a portion of the crown 110 (e.g., a knob) may protrude from the housing 102, and may define a generally circular shape or a circular exterior surface. The exterior surface of the crown 110 (or a portion thereof) may be textured, knurled, grooved, or may otherwise have features that may improve the tactile feel of the crown 110 and/or facilitate rotation sensing.

The crown 110 may facilitate a variety of potential user interactions. For example, the crown 110 may be rotated by a user (e.g., the crown may receive rotational inputs). Rotational inputs to the crown 110 may zoom, scroll, rotate, or otherwise manipulate a user interface or other object displayed on the display 114 (among other possible functions). The crown 110 may also be translated or pressed (e.g., axially) by the user. Translational or axial inputs may select highlighted objects or icons, cause a user interface to return to a previous menu or display, or activate or deactivate functions (among other possible functions). In some cases, instead of a crown that is rotatable and translatable by a user, the crown may be configured not to rotate or translate relative to the housing 102, but may nevertheless be configured to detect user interactions that are similar to rotational and translational inputs. For example, the watch 100 may sense, using touch sensors, force sensors, optical sensors, or the like, touch inputs or gestures applied to the crown 110. Such inputs may include a finger sliding along a surface of the crown 110, and a finger touching (or pressing on) an end face of the crown 110. In such cases, sliding gestures may cause operations similar to the rotational inputs, and touches (or presses) on an end face may cause operations similar to the translational inputs. As used herein, rotational inputs may include both rotational movements of the crown (e.g., where the crown is free to rotate), as well as sliding inputs that are produced when a user slides a finger or object along the surface of a crown in a manner that resembles a rotation (e.g., where the crown is fixed and/or does not freely rotate). In some cases, as noted above, haptic outputs may be produced in response to the detection of certain types of inputs applied to the crown 110. For example, a haptic output may be produced in response to detection of a particular rotational input (e.g., a partial rotation, such as 10° rotation, 20° rotation, 30° rotation, or any other suitable rotation), a translational input, or the like. In the case of crowns that are configured not to rotate or translate relative to a housing, a haptic output may be produced in response to detection of a sliding input applied to a surface of the crown, a touch input on an axial end of the crown, or a force (applied to the axial end of the crown) that satisfies a condition (e.g., exceeds a predetermined force corresponding to an actuation threshold).

The crown 110 may also include or define an electrode. For example, the crown 110 may be formed from or include a conductive material (e.g., a metal), which may in turn be conductively coupled to a biometric sensing system of the watch 100, such as an electrocardiograph sensing system. The electrocardiograph sensing system may use voltages detected by the electrode on the crown (as well as other electrodes of the watch 100, such as the electrodes 122 in FIG. 1B) to determine an electrocardiogram of the wearer. For example, the user may touch the electrode portion of the crown 110 to allow the electrode portion of the crown 110 to detect a voltage via the wearer's skin.

In some cases, instead of or in addition to an electrode integrated with the crown 110, an electrode may be positioned on a surface of the shell 104. For example, a conductive material (e.g., a metal, indium tin oxide, conductive nanowire coating, etc.) may be positioned on a side surface defined by a side wall of the shell 104, and a user may contact the conductive material (e.g., with a finger or another body part) to facilitate the detection and/or measurement of a voltage via the conductive material. Electrodes may also or instead be positioned on a front surface defined by a front wall of the shell 104. Electrodes mounted to a surface of the shell 104 may be coupled to the shell 104 in any suitable way and/or using any suitable technique. For example, the electrodes may be formed by plating or otherwise depositing a conductive material (e.g., a metal) onto a surface of the shell 104 (e.g., using chemical vapor deposition, plasma vapor deposition, electroless plating, or the like). As another example, a metal foil or other conductive film may be secured to the surface of the shell 104 using an adhesive or other bonding agent. An electrode that is coupled to a side wall, front wall, or other surface of a shell 104 may be coupled to a circuit within the housing (e.g., a voltage measuring circuit) in various ways. For example, a through hole may be formed through the shell 104, and a conductor (e.g., wire, flex circuit, etc.) may extend through the hole to conductively couple the external electrode to the internal circuit. As another example, the electrode may form a continuous conductor that extends along part of the exterior surface of the shell 104, around an edge of the shell 104, and along part of an interior surface of the shell 104. The portion extending along the interior surface of the shell 104 may be conductively coupled to a circuit within the device.

The watch 100 may also include other inputs, switches, buttons, or the like. For example, the watch 100 may include a button. The button may be a movable button (as depicted) or a touch-sensitive region of the housing 102. The button may control various aspects of the watch 100. For example, the button may be used to select icons, items, or other objects displayed on the display 114, to activate or deactivate functions (e.g., to silence an alarm or alert), or the like. As noted above, a haptic output may be produced in response to detection of an input applied to the button (or indeed any other input device or system associated with the watch 100). Buttons may be positioned on or along a side wall of the shell 104. For example, a button may be positioned next to the crown 110, or on a side of the watch 100 opposite the crown 110. In some cases, the watch includes multiple inputs, switches, buttons, or the like.

In cases where the watch 100 includes buttons, switches, crowns (e.g., the crown 110), the shell 104 may define through holes that allow components of the buttons, switches, crowns, and/or other components to pass through the shell 104 and access the interior volume of the watch 100. For example, a shaft portion of a crown may extend through a through hole defined through a side wall of the shell 104. The shaft portion may be coupled to one or more sensing systems within the watch 100 (e.g., rotation and/or translation sensing systems). An end or knob portion may be coupled to the shaft portion and define the component with which a user interacts (e.g., presses, rotates) to provide inputs to the watch 100 via the crown 110.

As described herein, some implementations of a watch or other electronic device may include touch- and/or force-sensitive side surfaces, optionally with displays underlying the side surfaces. These functionalities may be facilitated by the transparent, dielectric properties of the material of the shell 104 (e.g., glass). Accordingly, virtual buttons, crowns, sliders, or other input regions may be displayed on the side surfaces and interacted with by a user. Other types of sensors, such as biometric sensors, imaging sensors, or the like, may be configured to detect inputs on or through the side surfaces as well. Virtual input regions and other sensors may be implemented in conjunction with or instead of physical input components such as a button and a crown 110.

FIG. 1B depicts a rear of the watch 100. As shown, the chassis 106 defines a portion of the side surfaces of the watch 100, as well as a portion of the rear exterior surface of the watch 100. The watch 100 may also include a sensor cover 116 coupled to the chassis 106. The sensor cover 116 may cover a hole defined by the chassis 106. In some cases, the sensor cover 116 is positioned at least partially in the hole defined by the chassis 106. The sensor cover 116 may be configured to allow one or more sensors within the watch 100 to detect conditions external to the watch 100. For example, the sensor cover 116 may define transparent portions, such as sensor ports 118 and emitter ports 120. Together, the sensor ports 118 and emitter ports 120 may allow a biometric sensor system of the watch 100 to detect biometric and/or biological parameters of the wearer. For example, the sensor and emitter ports 118, 120 may facilitate the operation of a photoplethysmograph in which a light is emitted by an optical emitter through the emitter ports 120, and that light may be reflected (by the wearer's body) and detected, through the sensor ports 118, by an optical sensor. The sensor and emitter ports 118, 120 may be transparent portions of the sensor cover 116 (e.g., transparent to at least the particular wavelength(s) of light used by the sensor and emitter of the watch 100). In some cases, the sensor cover 116 may include a single piece of material (e.g., a monolithic structure) that defines both transparent portions (e.g., the sensor and emitter ports 118, 120) as well as other portions of the sensor cover 116 (e.g., non-transparent or opaque portions of the sensor cover 116 that surround the sensor and emitter ports 118, 120). The opaque portions of the sensor cover 116 may be defined by masked regions of the sensor cover 116, and the transparent portions of the sensor cover 116 (e.g., the sensor and emitter ports) may be defined by unmasked regions of the sensor cover 116.

In some cases, the sensor cover 116 may be an assembly or otherwise include multiple materials or components. For example, the sensor and emitter ports 118, 120 may be defined by lenses or other suitably transparent covers, windows, or other materials(s) positioned in openings in a carrier (e.g., the main structure of the sensor cover 116 that holds the sensor and emitter ports 118, 120). While FIG. 1B shows two round sensor ports 118 and two round emitter ports 120, more or fewer sensor and emitter ports 118, 120 may be used, and the ports may have shapes and/or positions that differ from those shown in FIG. 1B.

Other types of sensors may also or instead be integrated with the sensor cover 116. For example, electrodes 122 may be positioned on the sensor cover 116, and may be conductively coupled to components of a sensor system (e.g., an electrocardiograph sensing system) within the watch 100. The electrodes 122 may be a metal or other conductive material, and may be secured or applied to the sensor cover 116 in various ways. For example, the electrodes 122 may be plated, adhered, or bonded to the sensor cover 116, and may wrap around a side and along an interior surface of the sensor cover 116 so that the electrodes 122 may conductively couple a user's skin to a sensing system of the watch 100. Example configurations of the electrodes 122 are described herein. The watch 100 may include two electrodes 122, as shown, or more or fewer electrodes (e.g., one electrode, three electrodes, four electrodes, or more electrodes).

FIG. 1C is a side view of the watch 100. As shown in FIG. 1C, the shell 104 defines a first portion of the side exterior surface of the housing 102, and the chassis 106 defines a second portion of the side exterior surface of the housing. As shown, the shell 104 defines more than half of the height of the side surface, extending nearly the full distance from the front surface to the rear surface. In some cases, the side wall of the shell 104 extends about 50% of the distance from the front surface to the rear surface, about 60% of the distance from the front surface to the rear surface, about 70% of the distance from the front surface to the rear surface, about 80% of the distance from the front surface to the rear surface, about 90% of the distance from the front surface to the rear surface, or about 100% of the distance from the front surface to the rear surface.

Figure 2:
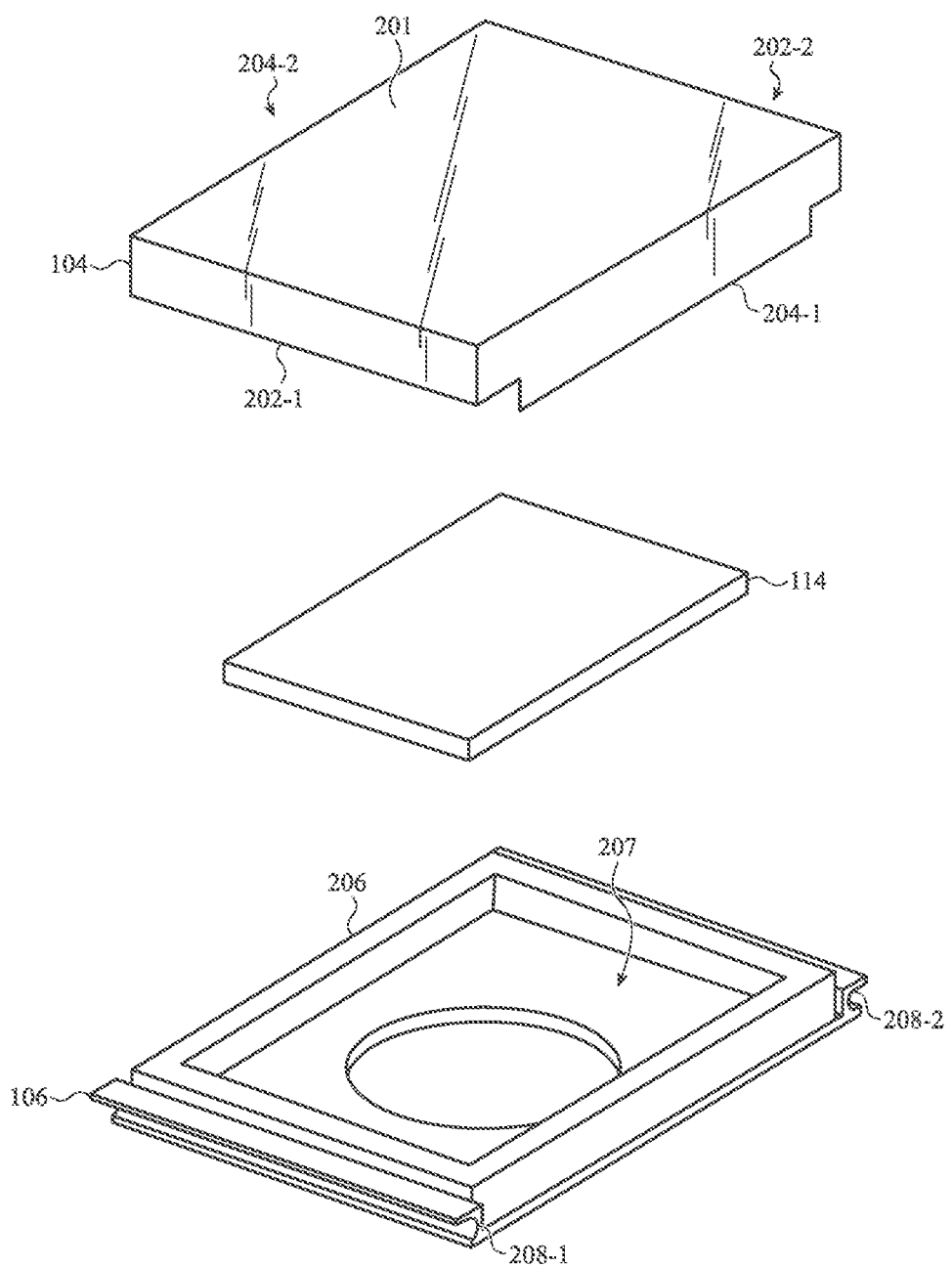
FIG. 2 depicts an exploded view of the electronic device of FIGS. 1A-1C.

FIG. 2 illustrates a partial exploded view of the watch 100 of FIGS. 1A-1C, showing the shell 104 removed from the chassis 106. The shell 104 defines a front wall 201 (also referred to herein as a top wall) that defines a front surface of the watch 100. The front wall 201 may also define a touch- and/or force-sensitive input surface of the watch 100, with which a user may interact to control operations of the watch 100.

The shell 104 further defines a first pair of side walls 202 (e.g., a side wall 202-1 and an opposite side wall 202-2) that extend rearward from the front wall 201, and a second pair of side walls 204 (e.g., a side wall 204-1 and an opposite side wall 204-2) that extend rearward from the front wall 201. The side walls of the second pair of side walls 204 may be longer than the side walls of the first pair of side walls 202. For example, the first pair of side walls 202 may be shorter than the second pair of side walls 204 due to the presence of band engagement features 208 (e.g., band engagement features 208-1, 208-2) on those same sides of the watch 100. In some examples, the side walls all have substantially the same length.

As shown in FIG. 2, the band engagement features 208 are defined by slots formed into the chassis 106, though this is merely one example band engagement feature. In other cases, band engagement features may be or may include lugs, holes, bars, protrusions, or other structures.

The chassis 106 may define an internal wall 206 that extends from a rear portion of the chassis 106. The internal wall 206 may extend around and at least partially define an internal volume 207 in which internal components of the watch 100 may be positioned. The internal wall 206 may extend towards the front of the watch 100 and may overlap the side walls 202 and 204, and may be secured to the interior surfaces of the side walls 202, 204, as described herein.

FIG. 2 also illustrates an example of the display 114, which may be covered by the shell 104 and may be configured to produce graphical outputs that are visible through a front wall of the shell 104. The display module 114 may also be configured to wrap or curve along one or more of the side walls of the shell 104 (which may be curved), and may be configured to display graphical outputs that are visible through the one or more side walls. In some cases, additional display modules may be configured to display graphical outputs that are visible through the side walls.

Figure 3A:
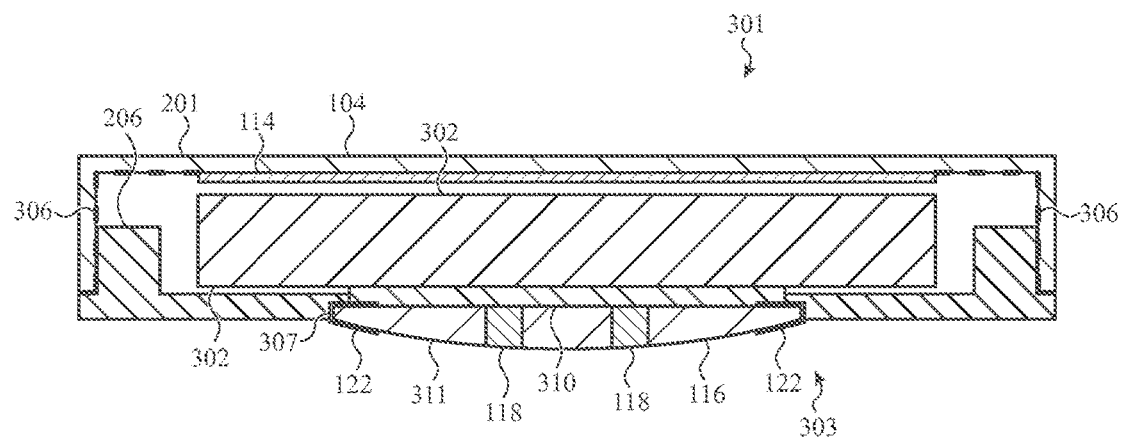
FIGS. 3A-3B depict partial cross-sectional views of example electronic devices.
Figure 3B:
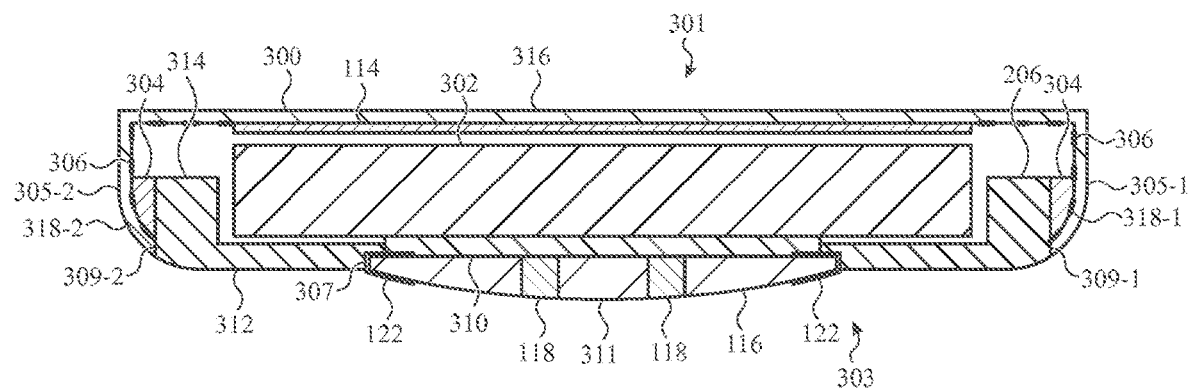

FIGS. 3A-3B are partial cross-sectional views of embodiments of the watch 100, viewed along line A-A in FIG. 1A. FIG. 3A shows an example configuration of the housing 102, which may be defined at least in part by the shell 104, the chassis 106, and the sensor cover 116. FIG. 3B shows another example configuration of the housing 102, which may be defined at least in part by a shell 300, a chassis 312, and the sensor cover 116. The housings defined by the shells and chassis in FIGS. 3A-3B may define an internal volume in which components such as the display 114, a sensor module 310, and other internal components 302 may be positioned. The internal components 302 may include components such as batteries, processors, memory, logic boards, battery charging circuitry (including wireless or inductive charging components such as inductive coils), wireless communication circuitry, antennas, or the like.

As shown in FIGS. 3A-3B, the side walls 204 (FIG. 3A) and 318 (FIG. 3B) each define a portion of a side surface of the watch 100, and the chassis 106 (FIG. 3A) and 312 (FIG. 3B) define a second portion of that side surface of the watch 100. As shown, however, the side walls each extend rearward more than half of the distance between the front surface of the watch 100 and the rear surface 303 of the watch. This may result in greater sealing as well as a more attractive appearance, as the seam between the shell and the chassis is positioned further away from the front surface of the watch 100.

Figure 4A:
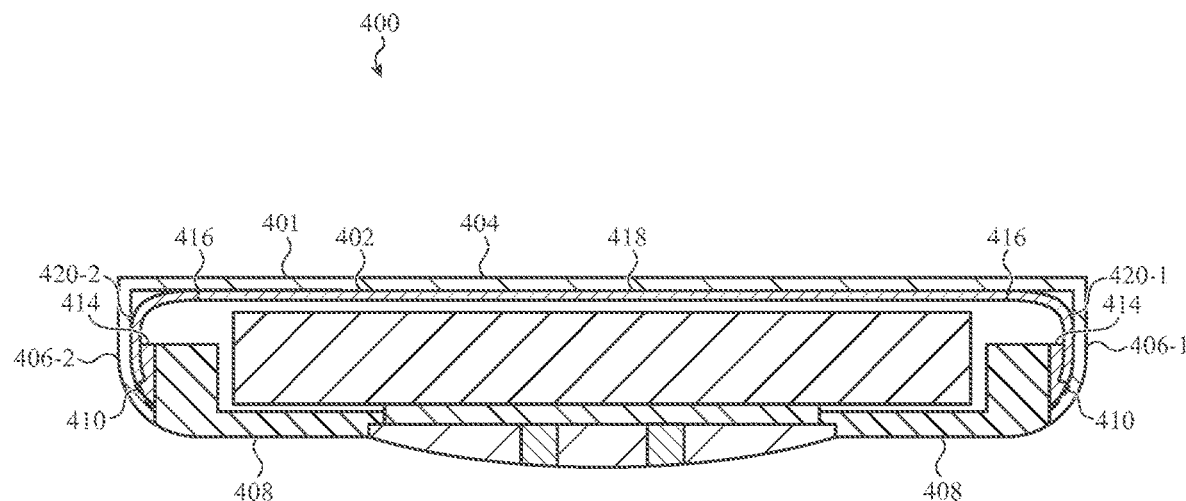
FIGS. 4A-4B depict partial cross-sectional views of example electronic devices.
Figure 4B:
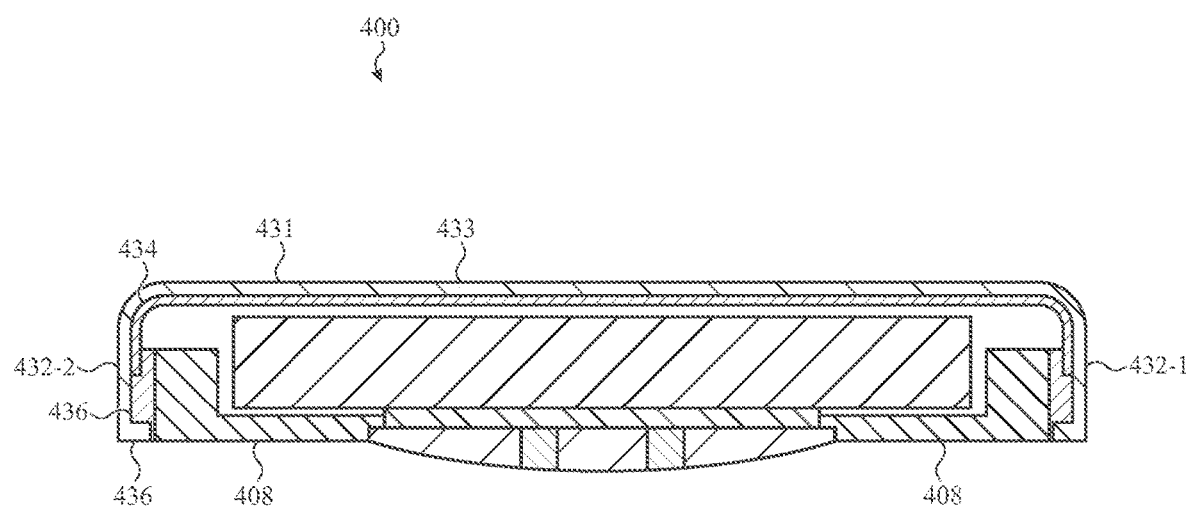

While FIG. 3A shows flat side walls 204, in some cases the side walls define a curved portion, such as a curve proximate the distal ends of the side walls (e.g., where the side walls 318 meet the chassis 312, as illustrated in FIG. 3B), a curve proximate the location where the front wall meets the side walls (as illustrated in FIG. 4B), and/or a continuous curvature that extends from the front wall of a shell to the ends of the side walls (e.g., a combination of the curvatures shown in FIGS. 3B and 4B). FIG. 3B illustrates an embodiment of the watch 100 in which a shell 300 defines a curve proximate the distal ends 309 of the side walls 318. Thus, the outermost points 305 (e.g., 305-1, 305-2) of the side surfaces of the watch 100 are defined by the shell 300, and the outermost points 305 of the curved side walls may visually obscure or hide the seam (at least in some viewing configurations).

FIG. 3B illustrates an example in which the side walls 318 define a curved portion proximate the distal ends 309 of the side walls 318, where the side walls 318 meet the chassis 312. In some cases, a curvature is also present where the front wall 316 meets the side walls 318 (e.g. similar to the curvature shown in FIG. 4B), such that a continuous curvature is defined along the side wall, extending from the front wall 316 to the distal ends 309 of the side walls 318. In such cases, the entireties of the exterior surfaces of the side walls may be curved (e.g., such that the side walls do not define flat or planar exterior surface portions). A continuously curved side wall may define an apex at its outermost point, which may visually obscure or hide the seam between the distal ends of the side walls and the chassis, similar to the configuration shown in FIG. 3A.

As noted above, a chassis may define an internal wall (internal wall 206 in FIG. 3A and internal wall 314 in FIG. 3B) that may overlap the side walls of the shell (e.g., side walls 204 in FIG. 3A and 318 in FIG. 3B (and also the side walls 202, FIG. 2). The internal walls may extend about a perimeter of the chassis, and may be composed of multiple wall segments (e.g., four wall segments, as shown in FIG. 2). The internal walls may resemble a rib or flange extending from a back wall defined by the chassis. The internal walls may be attached to the side walls of the shell in any suitable way, including adhesives, fasteners, or the like. In some cases, as shown in FIG. 3B, a gap may be defined between the internal wall 314 and the interior surfaces of the side walls 318. An adhesive 304 or other bonding agent may be positioned in this gap to secure the shell 300 to the chassis 312.

With reference to FIG. 3B, the adhesive 304 may form an adhesive bond with the side walls 318 and the internal wall 314, thereby retaining the shell 300 to the chassis 312. As used herein, adhesive bonds may refer to bonds formed as a result of chemical bonds, intermolecular forces (e.g., van der Waals forces), mechanical bonds (e.g., adhesive engaging with pores, textures, or other surface irregularities of the materials), electrostatic forces, and/or any other suitable adhesion mechanism.

In some cases, the shape of the interior surfaces of the side walls 318 may facilitate a mechanical interlock between the shell 300 and the chassis 312. For example, the curvature of the side walls 318 may define convex exterior surfaces and corresponding concave interior surfaces of the shell 300. The concave interior surfaces may define features that mechanically interlock with the adhesive 304 to retain the shell 300 to the chassis 312 and/or prevent the removal of the shell 300 from the chassis 312. More particularly, the distal ends 309 of the side walls 318 are further towards the center of the device than the outermost points 305 of the side walls 318. As such, when the adhesive 304 is hardened (e.g., cured, solidified, etc.), the distal ends 309 of the side walls 318 are mechanically interlocked with an undercut region of the adhesive 304, thereby inhibiting separation of the shell 300 from the chassis 312.

The shells 104, 300 may have a substantially uniform thickness. For example, a thickness of the side walls of a shell (e.g., side walls 202, 204, 318) may have substantially the same thickness as the front wall of the shell. The shell may have a thickness between about 1.5 mm and about 0.5 mm. In some cases, the thickness may be about 1.5 mm, about 1.25 mm, about 1.0 mm, about 0.75 mm, about 0.5 mm, or any other suitable thickness. In some cases, different portions of the shell may be thicker than others. For example, the distal ends of the shell (e.g., the free ends of the side walls), and/or the curved portions of the side walls, may be thicker than other portions of the shell.

While FIGS. 3A-3B illustrate physical engagement between a chassis and one pair of side walls (e.g., side walls 204, 318), it will be understood that the side walls 202, or any other side walls of a shell as described herein, may have the same or similar configuration as the side walls shown in FIGS. 3A-3B, and may use the same or similar structures and techniques to physically engage a shell with a chassis.

As described above, the watch 100 may include a display 114. The display 114 may be coupled to an interior surface of the front wall of the shell (e.g., front wall 201 in FIG. 3A or front wall 316 in FIG. 3B), or may otherwise be positioned within the housing of the watch 100 such that it can produce graphical outputs that are visible through the front wall. In order to define a boundary of an active area of the display 114 and/or prevent the visibility of internal components of the watch 100, an opaque mask 306 may be positioned along a front interior surface of the shell (as shown in FIGS. 3A and 3B). In some cases, the opaque mask 306 is positioned along all of the internal surface of the shell except the active display area (e.g., such that the opaque mask 306 defines an opaque boundary around a transparent portion of the shell through which the display is viewed). In some cases, the opaque mask 306 may be omitted from certain areas of the internal surface. For example, in cases where a display, sensor, or other component may require transparency or translucency, the opaque mask may be omitted from that particular area. The opaque mask 306 may be one or more layers of ink, dye, film, deposition layer (e.g., a layer of material deposited by a vapor or other deposition technique), coating, or the like.

As shown in FIGS. 3A-3B, the watch 100 also includes one or more sensors, represented by a sensor module 310. The sensor module 310 may not represent the exact size, location, or configuration of the sensors in the watch 100, but is intended more as a schematic illustration of the sensors. In some cases, the sensor module 310 may include sensing systems (or components thereof) such as a photopletheysmograph, an electrocardiograph, a pulse oximeter, or other biometric or other sensing systems. Biometric sensing systems may be configured to detect and/or measure biological parameters of a wearer. Such sensing systems may include components such as voltage sensors, optical emitters, optical sensors, cameras, or any other suitable components to facilitate biometric or other sensing. The sensing systems of the watch 100 may access or otherwise interact with the outside environment via the sensor cover 116, which may be positioned in an opening 307 in the chassis.

The sensor cover 116 may be formed from a transparent material such as glass, ceramic, sapphire, metal, polymer, a composite (e.g., fiber-reinforced polymer), or the like. In some cases, the sensor cover 116 may be formed from an opaque material and may define openings in which transparent materials or components are positioned, as described herein.

As noted above, the sensor cover 116 may define transparent portions, such as sensor ports 118 and emitter ports 120 (FIG. 1B). FIGS. 3A and 3B illustrate one example configuration of the sensor cover 116 in which the sensor ports 118 are defined by transparent or translucent materials positioned in openings in a carrier member 311. The carrier member 311 may be formed of an opaque material, or it may be formed of a transparent material and include a mask (e.g., dye, ink, film, etc.) to produce an opaque appearance.

In other cases, instead of separate materials or components positioned in openings in the carrier member 311, the sensor ports 118 may be defined by transparent portions of a monolithic carrier member 311. In such cases, the carrier member 311 may be formed of a transparent material and may include a mask (e.g., dye, ink, film, etc.) to define opaque regions in areas other than the sensor ports 118 (e.g., surrounding the sensor ports 118). While FIGS. 3A-3B illustrate example configurations of the sensor ports 118, the same and/or similar configurations may apply to the emitter ports 120 as well. A sensor cover 116 may also use inset transparent materials to provide optical access for some sensor components, and use monolithic transparent regions of a carrier to provide optical access for other sensor components.

As noted above, electrodes 122 may be positioned on the sensor cover 116, and may be conductively coupled to an electrocardiograph sensing system (represented by the sensor module 310). The electrodes 122 may be a metal or other conductive material. The electrodes 122 may wrap around an edge of the sensor cover 116 to define an exterior portion and an interior portion of each electrode. The exterior portion may define part of the rear surface of the watch 100 and may be positioned so that it is likely to be in contact with a user when the watch 100 is being worn. The interior portion of an electrode may be conductively coupled to a voltage sensor or other component or system, and a voltage measurement from the electrode (optionally along with voltage measurements from other electrodes on the sensor cover 116, the crown 110, and/or elsewhere on the device) may be used by an electrocardiograph to determine an electrocardiogram of the wearer.

FIG. 4A depicts an example cross section of a watch 400, which may be an embodiment of the watch 100. The description of the various components and elements of the watch 100 may also be applicable to the watch 400 depicted in FIG. 4A. A redundant description of some of the components is not repeated herein for clarity.

Whereas the watch 100 includes a display that is viewable through the front wall 404 of the shell, the watch 400 includes a display 402 that is viewable through the front wall 404 of a shell 401 (which may be the same as or similar to the shell 104) as well as through the side walls 406 of the shell 401. For example, the display 402 may define a first portion 418 that is adjacent the front wall 404 of the shell 401 (or otherwise viewable through the front wall), as well as second portions 420 that are adjacent the side walls 406 of the shell 401 (or otherwise viewable through the side walls). The display 402 may be a single display component that is bent, flexed, or otherwise formed to the contour of the interior surfaces of the shell 401. In other cases, the display 402 may include separate display components. For example, one physical display stackup may be used to display graphical outputs through the front wall 404 of the shell 401, while a separate physical display stackup may be used to display graphical outputs through the side wall 406-1, and yet another separate physical display stackup may be used to display graphical outputs through the side wall 406-2. The boundary between the physical display stackups may be at the line 416, though this is merely one example. In some cases, the stackup that is viewable through the front wall 404 is substantially planar, and the stackups that are viewable through a side wall are non-planar (e.g., curved). In cases where a single display stackup is used to display graphical outputs through both the front wall and one or more side walls, the lines 416 may represent a functional boundary between "front facing" and "side facing" display regions. Further, while the watch 400 shows displays adjacent two side walls, this is merely one embodiment, and a watch as described herein may have displays that can display graphical outputs on one, two, three, or four side walls of the device.

The watch 400 may also include a mask 410 along some portions of the interior surface of the shell 401. For example, the mask 410 may be positioned along a portion of the shell 401 that is in contact with an adhesive 414 (where the adhesive 414 attaches the shell 401 to a chassis 408, in a manner similar to the adhesive 304, FIG. 3B). The mask 410 may also be positioned along other portions of the shell 401, such as to mask or occlude boundaries between different display stackups (e.g., to cover a gap between components at line 416). The mask 410 may be an opaque material (e.g., one or more layers of ink, dye, film, etc.) that is attached to an inner surface of the shell 401.

FIG. 4B illustrates another example of the watch 400, in which a shell 431 defines a curved surface where the side walls 432 meet the front wall 433. The curved surface may have a corresponding curved (e.g., concave) interior surface, that a display 434 may be proximate or attached to. In some cases, the display 434 is adhered to the interior surface of the shell 431, including along an interior surface of the front wall 433, the interior surface of the side walls 432, and the interior concave surface between (and joining) the front wall 433 and the side walls 432. As the side walls 432 in FIG. 4B do not define a curve at their distal ends, the side walls 432 may define flanges 435, which may engage an adhesive 436 (in a manner similar to the sidewalls 406 and adhesive 414 in FIG. 4A) to retain the shell 431 to the chassis 408.

Figure 4C:
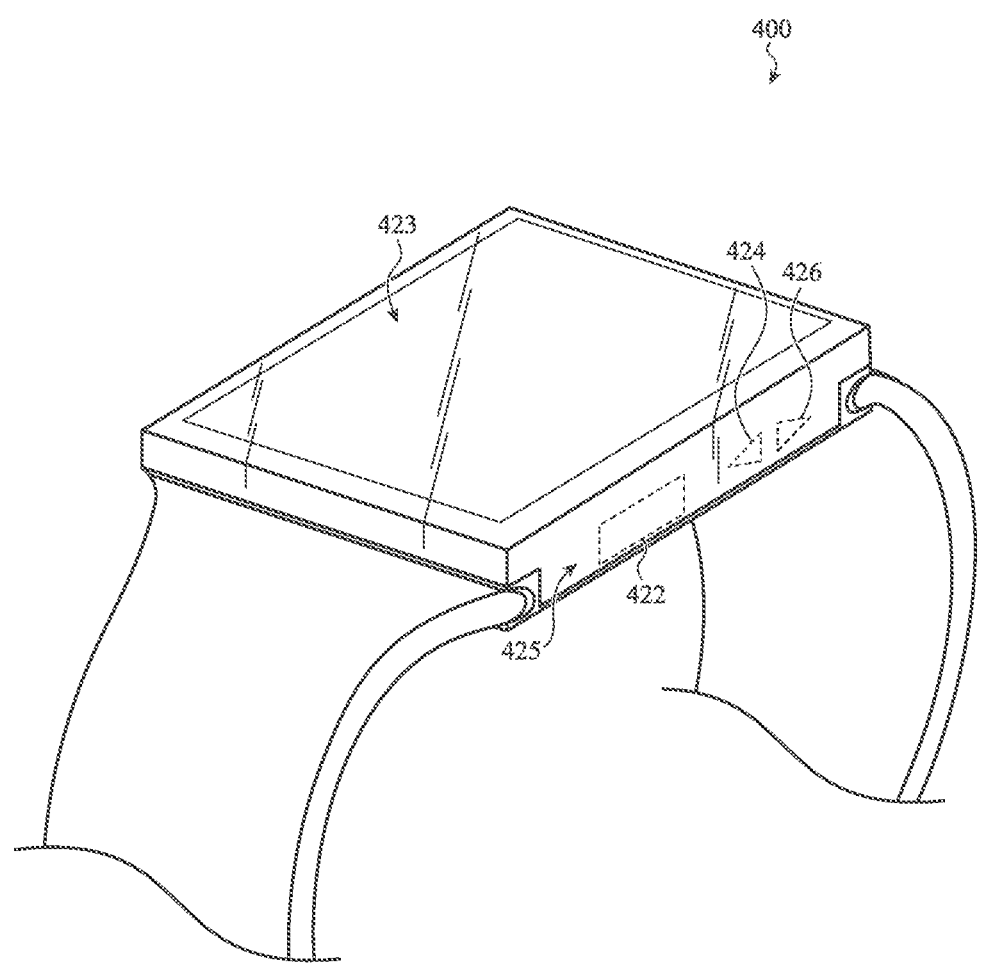
FIGS. 4C-4D depict perspective views of the electronic device of FIG. 4A.
Figure 4D:
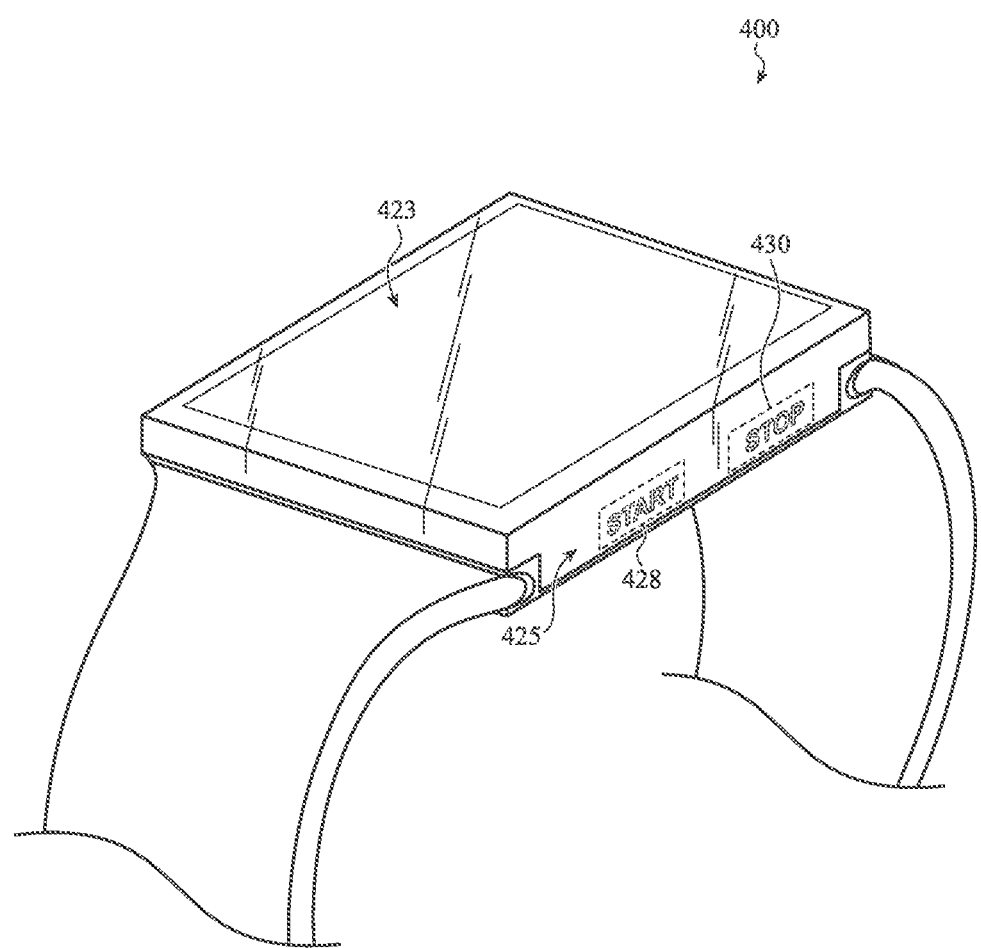

FIGS. 4C-4D illustrate the watch 400 of FIG. 4A with graphical outputs displayed through a side wall by a side-facing portion of the display 402 (e.g., a second portion 420-1 of the display 402). Notably, the display 402 can produce various types of graphical outputs on the sides of the device, and can dynamically change or vary the graphical outputs based on factors such as time of day, an active application of the watch 400, a current activity of the wearer (e.g., exercise, listening to music, watching video media, sleeping, working, running, swimming, etc.), or any other suitable factor. Further, the watch 400 may include touch sensing systems, force sensing systems, or other types of sensing systems that can detect inputs applied to the front and/or side walls of the watch 400 (e.g., touch inputs applied by a user). Accordingly, the graphical outputs displayed on the sides of the watch 400 may be buttons, sliders, or other affordances.

FIG. 4C, for example, illustrates the watch 400 while displaying a first set of graphical outputs on a side display region 425 of the watch 400. For example, the graphical outputs may include buttons 422, 424, and 426, where the buttons 424, 426 are configured as directional buttons (e.g., arrows). The buttons 422, 424, 426 may be used to navigate within a graphical user interface that is displayed on a front display region 423 of the watch 400 (e.g., to move a cursor or other "active" element indicator with the directional buttons, and select particular affordances, functions, or other elements with the button 422). The directional buttons 424, 426 may control functions such as volume (e.g., of a speaker of the watch 400 or of other devices that may be controlled by the watch such as a phone, headphones, a tablet computer, a wireless speaker unit, or the like).

FIG. 4D illustrates the watch 400 while displaying a second set of graphical outputs on the side display region 425 of the watch 400. For example, the graphical outputs in FIG. 4D may include a start button 428 and a stop button 430. The watch 400 may transition from the first set of graphical outputs (e.g., those shown in FIG. 4C or any other graphical outputs or even a blank side display region) to the second set of graphical outputs upon activation of an application, detection of an activity of the wearer, or the like. For example, the start and stop buttons 428, 430 may control a stop watch or other fitness tracker, or it may control music or other media playback.

The buttons shown in FIGS. 4C-4D are merely examples of buttons, affordances, images, or other graphical outputs that may be displayed on a side display region of a watch 400. Other types of graphical outputs may be displayed on a side display region of a watch depending on user settings, detected conditions of the watch and/or of the user, or based on other factors or triggering events.

In some cases, other types of sensing systems may be integrated with or otherwise use the side walls of a watch as input surfaces. For example, a fingerprint sensor may be positioned within the watch 400 adjacent a side wall of the shell 401. A user may place a finger on the side wall in the region of the fingerprint sensor (which may be graphically indicated by a graphical output of a display, a marking on the shell 401, or the like), and the fingerprint sensor may capture an image or other representation of a user's fingerprint to authenticate the user and, optionally, unlock the watch 400 and/or other devices with which the watch 400 can communicate. In some cases, cameras, optical sensors, photoplethysmographs, blood oxygen sensors, ambient light sensors, depth sensors, or the like, may be positioned within the watch 400 and may be configured to access the external environment using the transparency of the shell 401 (including the side walls of the shell 401).

Figure 5A:
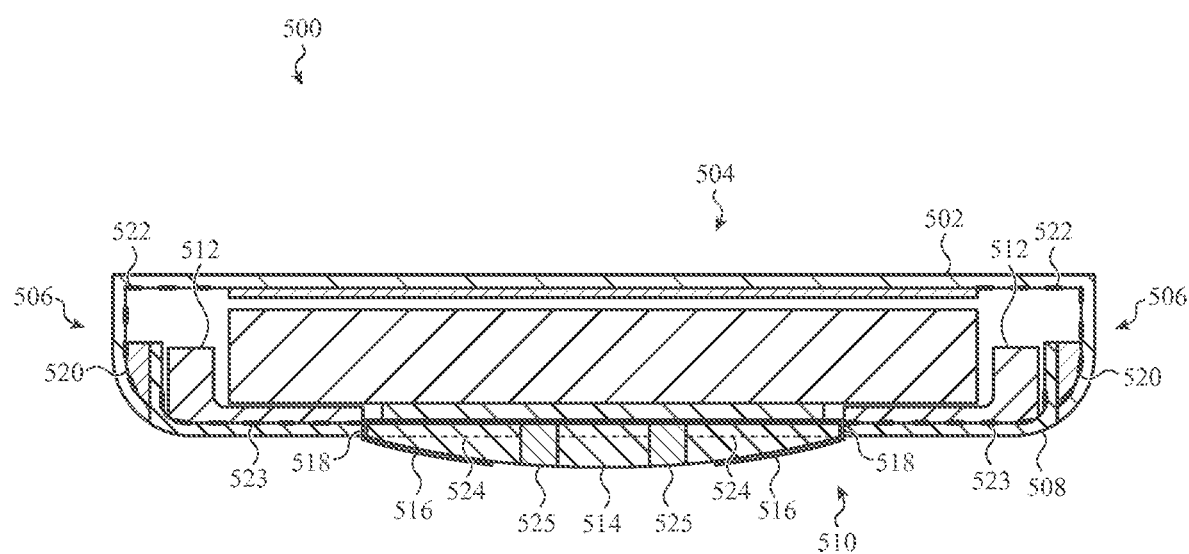
FIG. 5A depicts a partial cross-sectional view of another example electronic device.
Figure 5B:
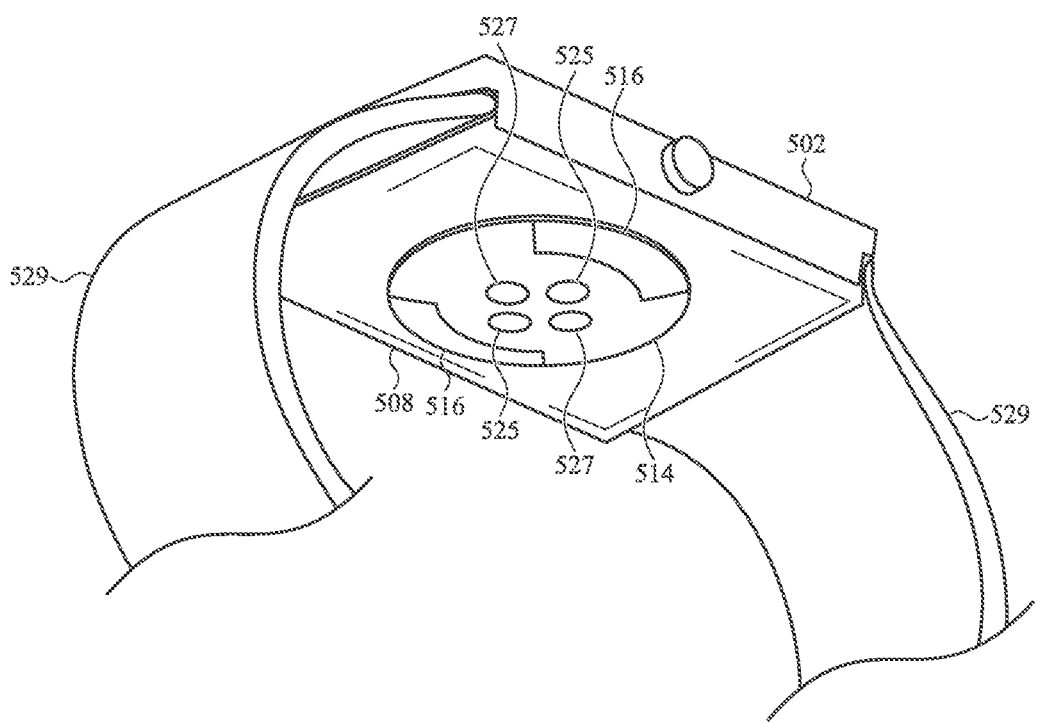
FIG. 5B depicts a rear perspective view of the electronic device of FIG. 5A.
Figure 5C:
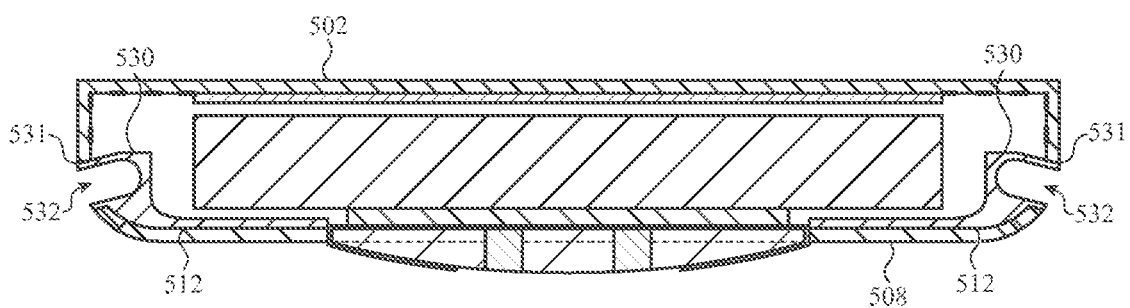
FIG. 5C depicts a partial cross-sectional view of the electronic device of FIG. 5A.

In some cases, a watch may include a glass (or other transparent dielectric material) shell that defines a front surface and at least a portion of the side surfaces of the watch, similar to those described with respect to FIGS. 1A-4D, as well as a glass (or other transparent dielectric material) component that defines a rear surface and another portion of the side surfaces of the watch. FIGS. 5A-5C illustrate an example watch 500 that includes a first shell 502 (e.g., a first glass shell) that defines a top or front surface 504 of the watch 500, as well as a first portion of the side surfaces 506 of the watch 500, and a second shell 508 (e.g., a second glass shell) that defines a portion of a rear surface 510 as well as a second portion of the side surfaces 506.

The second shell 508 may be attached to the first shell 502 via an adhesive 520, which may be the same as or similar in materials, function, etc., to the adhesives described elsewhere herein (e.g., the adhesive 304, FIG. 3B). The first shell 502 and the second shell 508 may include masks 522, 523 (respectively), which may be positioned along an interior surface of the first and second shells 502, 508 (e.g., along a portion of the front interior surface and side interior surfaces (which may have concave curvatures) of the first shell 502, and along a portion of a back interior surface). In some cases, the masks are opaque and mask, cover, or occlude internal components. Openings in the masks (or areas where the mask is not applied) may define display regions or other windows, openings, or transparent regions for displays, sensors, or other components or functions. The masks 522, 523 may be an opaque material (e.g., one or more layers of ink, dye, film, etc.) that is attached to an inner surface of the shells.

The watch 500 may also include a frame 512 within the watch 500. The frame 512 may act as a chassis or main structural component of the watch 500 to which other components may be coupled. For example, the second shell 508 may be secured to the frame 512 (e.g., via fasteners, adhesives, mechanical interlocks, or any other suitable attachment technique). Other components may also be coupled to the frame 512 (e.g., logic boards, processors, batteries, sensor modules, displays, memory, battery charging circuitry, etc.). The frame 512 may be formed of metal (e.g., aluminum, steel, an alloy, etc.), a polymer, a composite, or any other suitable material.

The second shell 508 may also define a sensor cover 514. The sensor cover 514 may be configured to allow one or more sensors within the watch 500 to detect conditions external to the watch 500. For example, the sensor cover 514 may define transparent portions, such as sensor ports 525 and emitter ports 527 (FIG. 5B) which may be the same as or similar to the sensor and emitter ports 118, 120 described herein. A redundant description of some of the components is not repeated herein for clarity. The sensor cover 514 may protrude outwardly from the rear of the watch so that it can press against the skin on the wrist of a user, which may help facilitate positive contact between the sensor cover 514 and the user's skin, thereby improving the effectiveness of biometric sensors of the watch.

Similar to other watches described herein, electrodes 516 may be positioned on the sensor cover 514, and may be conductively coupled to components of a sensor system (e.g., an electrocardiograph sensing system) within the watch 500. The electrodes 516 may be a metal or other conductive material, and may be secured or applied to the sensor cover 514 in various ways. For example, the electrodes 516 may be plated, adhered, or bonded to the sensor cover 514, and may extend through holes 518 formed through the sensor cover 514 (or formed through the second shell 508 more generally) so that the electrodes 516 may conductively couple a user's skin to a sensing system of the watch 500. The watch 500 may include two electrodes 516, as shown, or more or fewer electrodes (e.g., one electrode, three electrodes, four electrodes, or more electrodes).

In some cases, as shown in FIG. 5A, a sensor cover 514 may protrude somewhat from a surrounding region of the rear surface 510. The protrusion of the sensor cover 514 may be formed by a region of the second shell 508 that has an increased thickness relative to a region of the second shell 508 that surrounds or is adjacent the sensor cover 514. For example in the case of a glass second shell 508, the increased thickness may be formed by forming a single monolithic piece of glass such that the piece of glass defines the increased thickness region, or it may be formed by applying one or more additional layers of glass to the second glass shell 508. FIG. 5A illustrates an example location of a seam or boundary 524 where an additional layer of glass (or other suitable material) has been applied to a main portion of the second shell 508 to define the increased thickness region of the sensor cover 514. The layer of glass may be attached to the main portion of the second shell 508 in any suitable way, such as with an adhesive, by direct fusion of the layer to the main portion (e.g., via heat and pressure applied to the layer and the main portion), laser welding, or by any other suitable technique. In other cases, the protrusion may be formed by a curved region formed in a region of the second shell 508 that otherwise has a substantially uniform thickness (e.g., such that a concave recess is defined along the interior surface and a convex bump is defined along the exterior surface of the second shell 508).

FIG. 5B shows a rear perspective view of the watch 500. As shown in FIG. 5B, the rear surface 510 of the watch may be a substantially continuous piece of glass (with the exception of the electrodes 516, if equipped, and the lenses, windows, or other inset members for emitter and receiver ports, if equipped). FIG. 5B also illustrates a watch band 529 attached to the watch housing via watch band engagement features, as described in greater detail with respect to FIG. 5C.

FIG. 5C is a partial cross-sectional view of the watch 500, viewed along a line similar to line B-B in FIG. 1A. FIG. 5C illustrates one example configuration in which watch band engagement features are defined by the frame 512. For example, the frame 512 may define structural segments 530 that extend through an opening 531 in the first shell 502 (and/or the second shell 508, depending on the particular structural configuration of the shells). The structural segments 530 may define watch band engagement features 532 to which the watch band 529 (FIG. 5B) may be coupled. As shown, the watch band engagement features 532 include slots that receive an end of the watch band 529, though this is merely one example embodiment. In other cases, the watch band engagement features 532 may be bars, fasteners, threaded holes, lugs, or any other suitable structure for coupling a watch band to the watch 500. One potential advantage of the configuration shown in FIG. 5C is that any loads from the watch band 529 are directly coupled to an internal structural component (e.g., the frame 512), rather than the shells 502, 508. This may facilitate the use of thinner material (e.g., glass) for the shells, or otherwise help prevent or reduce damage to the shells.

In some cases, band engagement features may be coupled directly to a shell. FIGS. 6A-6D illustrate an example watch 600 in which band engagement features (specifically, lugs) may be attached directly to an exterior surface of a shell that defines a top and side surfaces of the watch 600.

Figure 6A:
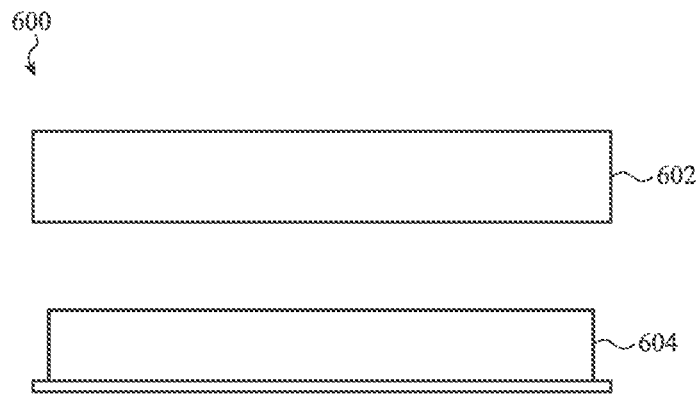
FIGS. 6A-6C depict another example electronic device.

FIG. 6A, for example, shows a portion of a watch 600 with the shell 602 separated from a chassis 604. The shell 602 may define a top or front wall, and four side walls, and the chassis 604 may define an internal wall that overlaps the side walls and is configured to be attached to the side walls of the shell 602. Whereas some shells described herein may have side walls of different lengths, the four side walls of the shell 602 may have substantially the same lengths. More particularly, the shorter side walls of other shells described herein may be configured to accommodate a watch band engagement feature. Because the watch band engagement features of the watch 600 are attached directly to the shell 602, the side walls of the shell 602 may all be the same or substantially the same length. Of course, side walls of different lengths may be used.

Figure 6B:
Figure 6C:
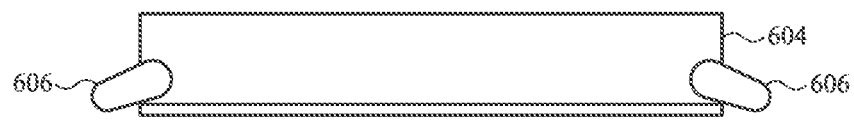
Figure 6D:
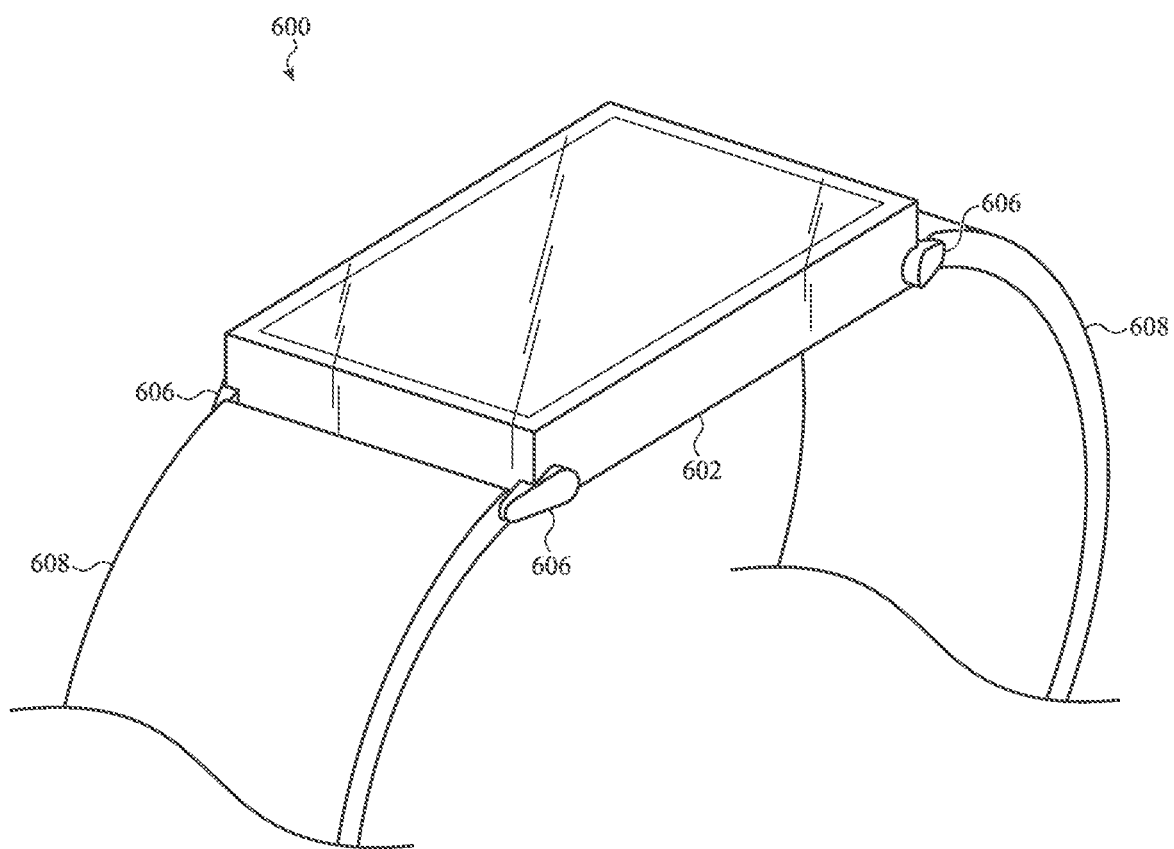
FIG. 6D depicts a perspective view of the electronic device of FIGS. 6A-6C.

FIG. 6B shows the watch 600 with the chassis 604 and the shell 602 attached to one another, and with a set of band engagement features 606 shown separated from the shell 602. FIG. 6C shows the watch 600 with the band engagement features 606 coupled to the shell 602. FIG. 6D is a perspective view of the watch 600 with the band engagement features 606 attached to the shell 602 and a watch band 608 coupled to the watch housing via the band engagement features 606. The watch band 608 may be coupled to the band engagement features 606 in any suitable manner. For example, the band engagement features 606 may define holes into which a spring bar (or any other suitable bar, rod, or other member) may extend to define a bar to which the band 608 may attach. The band engagement features 606 may be formed of any suitable material. For example, they may be formed from metal, metal alloys, glass, polymer, ceramic, or the like.

The band engagement features 606 may be attached to the shell 602 in various ways. For example, the band engagement features 606 may be attached to the shell 602 via adhesives, fasteners, fusion bonding, mechanical interlocks, or the like. In some cases, the band engagement features 606 may be formed of glass and may be attached to the shell 602 by fusing the glass of the band engagement features 606 to the glass of the shell 602. In some cases, instead of attaching separate band engagement features 606 to the shell 602, the band engagement features 606 may be integrally formed with the shell 602 (e.g., the shell 602 and the band engagement features 606 may be formed as a single monolithic structure).

In some cases, the band engagement features 606 may be secured to the chassis 604 instead of the shell 602. In such cases, holes may be defined through the shell 602, and the band engagement features 606 may be secured to the chassis 604 through the holes. The chassis 604 may also define holes (e.g., threaded holes), and the band engagement features 606 may be secured to the chassis 604 via fasteners (e.g., threaded fasteners) that engage the holes in the chassis 604. Other techniques for securing the band engagement features 606 to the chassis 604 are also contemplated.

As described herein, a shell may be attached to a chassis via an adhesive that is positioned in a gap defined between overlapping portions of an internal wall of the chassis and side walls of the shell. Any suitable type of adhesive may be used to attach a chassis to a shell, including but not limited to thermoset adhesives, thermoplastic adhesives, epoxies, resins, or the like.

Figure 7A:
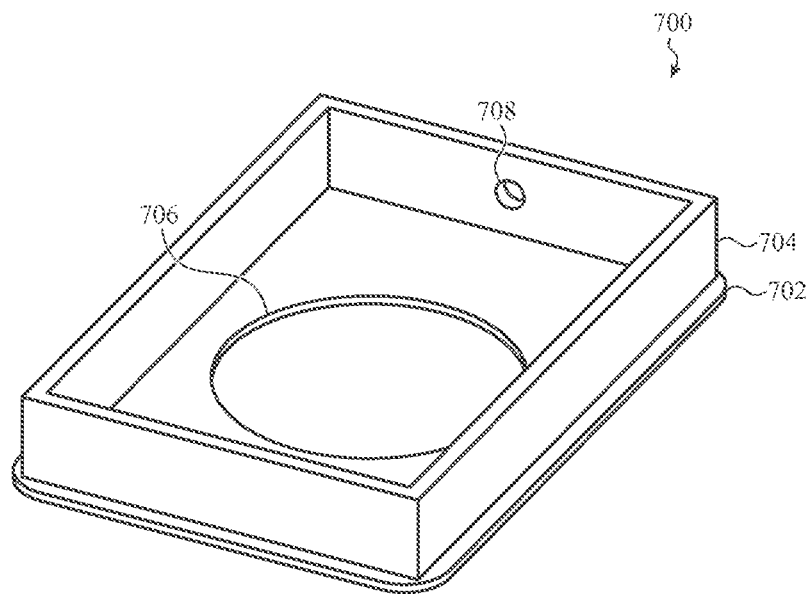
FIG. 7A depicts a perspective view of a chassis for an electronic device.
Figure 7B:
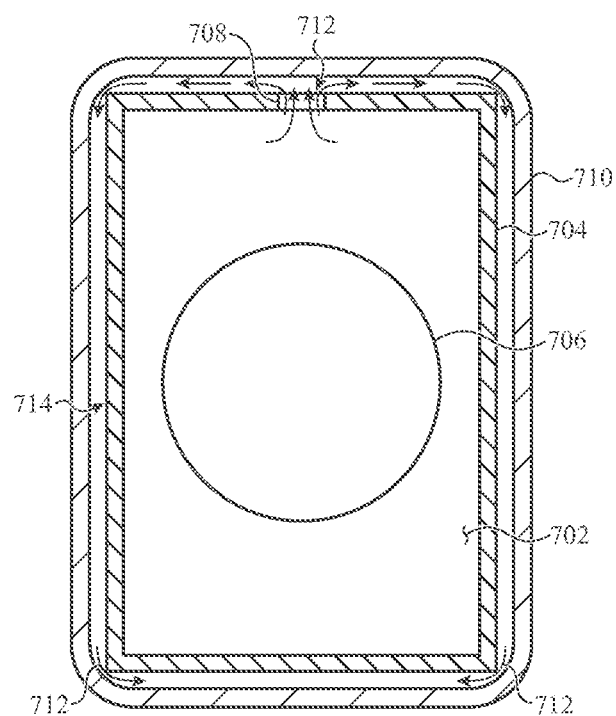
FIG. 7B depicts a partial cross-sectional view of a chassis and a shell for an electronic device.

FIGS. 7A-7B illustrate example structures and techniques that may be used to introduce the adhesive or other bonding agent into the gap. FIG. 7A, for example, illustrates an example chassis 700, which may be an embodiment of other chassis described herein (e.g., the chassis 106, 408, 604, etc.).

The chassis 700 may define a rear wall 702 and a wall 704 (e.g., an internal wall, such as the internal wall 206) extending from the rear wall, which may define a portion of a rear surface of the watch in which the chassis 700 is used. The chassis 700 may also define a hole 706 in the rear wall 702. The hole 706 may be adapted to receive a sensor cover, such as the sensor cover 116 described above, and may facilitate access to the external environment by sensor systems in the watch. The chassis 700 may also define an adhesive entry port 708. The adhesive entry port 708 may be through the hole that extends through the wall 704 and communicates with the gap between the wall 704 and a side wall of a shell. As shown, the adhesive entry port 708 is formed through the wall 704, though it may be formed through any portion of the chassis 700 that communicates with the gap. Moreover, while one adhesive entry port is shown, the chassis 700 may include additional adhesive entry ports as well to facilitate introduction of an adhesive into the gap. The chassis 700 may also include vent ports to allow air to escape the gap as adhesive is flowed into the gap.

FIG. 7B is a partial cross-sectional view of the chassis 700 and a shell 710 (as viewed along line C-C in FIG. 1A), after the shell 710 and the chassis 700 are assembled so that they can be adhered together. As shown in FIG. 7B, a gap 714 may be defined between an interior surface of the side wall of the shell 710 and the internal wall 704 of the chassis 700. Once the shell 710 and the chassis 700 are in a desired position relative to one another, an adhesive may be introduced into the gap 714 through the adhesive entry port 708, as indicated by flow lines 712. The adhesive may flow into the gap 714 and around the internal wall 704 such that it occupies at least a portion of the gap 714. The adhesive may then be allowed to cure or harden, thereby securing the shell 710 to the chassis 700.

The shell 710 and the chassis 700 may be adhered to one another before all of the internal components of the device are positioned in the internal cavity. In such case, components may be positioned in the device by passing them through the hole 706 in the rear wall 702 of the chassis 700.

FIGS. 8A-8D illustrate partial cross-sectional views of shells and chassis, showing various configurations and techniques for delivering and containing the adhesive to the desired locations. The cross-sectional views in FIGS. 8A-8D are viewed along a line similar to the line A-A in FIG. 1A.

Figure 8A:
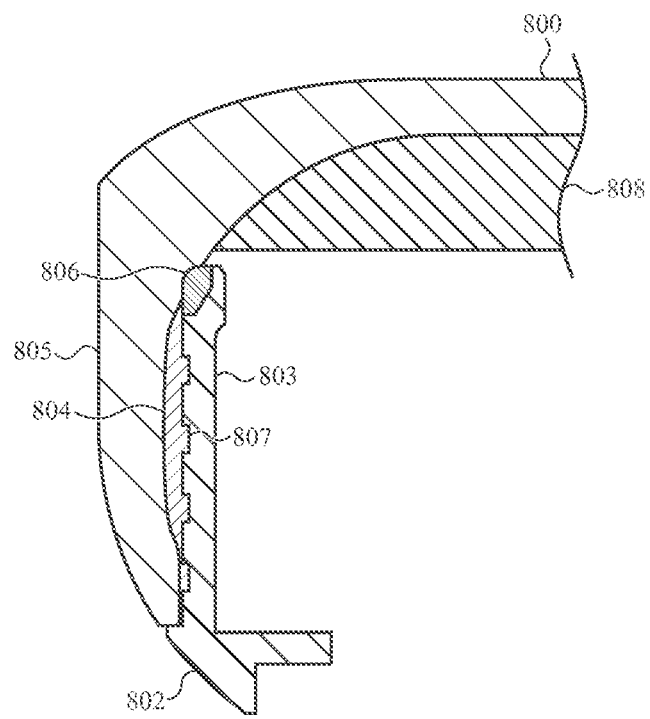
FIGS. 8A-8D depict partial cross-sectional views of example electronic devices.

FIG. 8A, for example, includes a shell 800 and a chassis 802 (which may be embodiments of the shell 104 and the chassis 106). As described herein, the chassis defines an internal wall 803 that overlaps a side wall 805 of the shell 800, and a gap is defined between the internal wall 803 and the interior surface of the side wall 805. An adhesive 804 has been introduced into the gap to secure the shell 800 and the chassis 802 together, as described herein. For example, the adhesive 804, in a flowable state, may have been introduced into the gap through a hole in the chassis 802. FIG. 8A also illustrates example engagement features 807 that may be formed on an outward-facing side of the side wall 805. The engagement features 807 may be configured to mechanically engage and/or interlock with the adhesive 804 to help retain the adhesive 804 to the internal wall 803, thereby contributing to the mechanical coupling between the shell 800 and the chassis 802. The engagement features 807 are illustrated as channels extending along the internal wall 803, though other features are also contemplated, such as holes, textures, dovetails, protrusions, bumps, recesses, dimples, posts, or the like.

In order to contain the adhesive 804 in the gap during the introduction of the adhesive 804, a compliant member 806 may be positioned between and in contact with the internal wall 803 of the chassis 802 and an interior surface of the side wall 805 of the shell 800. The compliant member 806 may be an elastomeric or deformable polymer or other material that can be compressed between the shell 800 and the chassis 802 to cause the compliant member 806 to conform to the shape of the surfaces it contacts and to form a seal therebetween. The compliant member 806 may be an o-ring, a foam that is applied to the chassis 802, or any other suitable sealing material or component. The compliant member 806 (and any other compliant members described herein) may be formed from any suitable material, such as silicone, nitrile, rubber, Buna N, or the like.

The compliant member 806 may help contain the adhesive 804 in the gap between the shell 800 and the chassis 802 during introduction of the adhesive 804. This may help ensure that the adhesive 804 fills the gap, rather than simply spilling out into the interior of the device and/or contacting a display stack 808. The compliant member 806 may be secured to the internal wall 803 of the chassis 802 (e.g., via adhesive, self-adhesion, mechanical means, etc.) so that it is retained in position during assembly and during introduction of the adhesive 804. The compliant member 806 may also act as an environmental seal to help inhibit the ingress of liquid or other contaminants (e.g., should there be any gaps in the adhesive 804 or if the adhesive 804 otherwise may not provide environmental sealing).

Figure 8B:
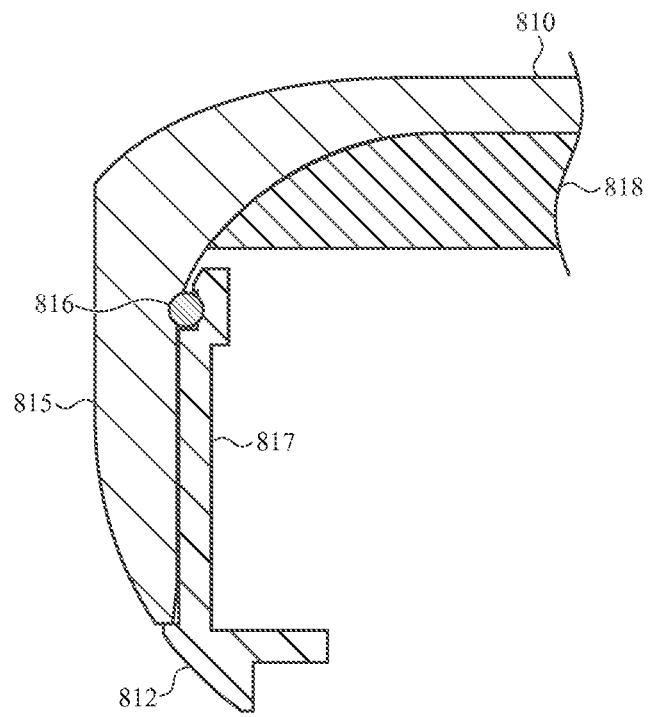

FIG. 8B illustrates another example configuration of a shell 810 and a chassis 812. In this example, a side wall 815 of the shell 810 may not define a concave interior surface, and instead may have an increased thickness (e.g., relative to a top or front wall of the shell 810), and may define a substantially planar interior surface. The chassis 812 may define an internal wall 817, and a compliant member 816 may be positioned between and in contact with the chassis 812 and the side wall 815 of the shell 810.

The increased thickness of the side wall 815 may result in little or no gap between the interior surface of the side wall 815 and the internal wall of the chassis 812. Accordingly, in some cases, little or no adhesive may be introduced in the gap, and the shell 810 may be secured to the chassis 812 using mechanical interlocks, fasteners, or other materials and/or techniques. In other cases, an adhesive, which may have a lower viscosity than other adhesives, may be introduced into the gap to secure the shell 810 to the chassis 812. The compliant member 816, which may otherwise be the same as or similar to the compliant member 806, may inhibit ingress of liquids or other contaminants into the interior of the watch. The watch may also include a display stack 818.

Figure 8C:
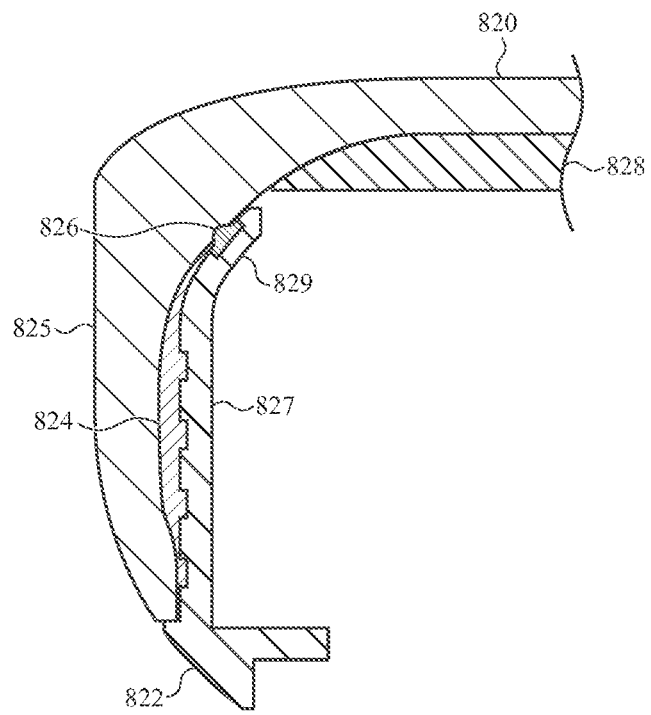

FIG. 8C illustrates another example configuration of a shell 820 and a chassis 822. In this example, the internal wall 827 defines a flange portion 829. The flange portion 829 may extend at an angle from the main portion of the internal wall 827 (e.g., the vertical portion, as oriented in FIG. 8C) and may have a curve, angle, contour, or shape that is the same as or otherwise conforms to the curve, angle, contour, or shape of the side wall 825 of the shell 820. The flange portion 829 may be positioned closer to the interior surface of the side wall 825, thus forming an area where the gap between the side wall 825 and the internal wall 827 is reduced (relative to other areas of the gap). This may increase the effectiveness of the compliant member 826, as the smaller gap may reduce the amount and/or pressure of the adhesive 824 on the compliant member 826 during the adhesive introduction process. This may help ensure that the adhesive 824 fills the gap, rather than simply spilling out into the interior of the device and/or contacting a display stack 828. The flange portion 829 may also increase the strength and/or durability of the assembled device, as the flange portion 829 produces a larger contact area between the chassis 822 and the shell 820 in the event of a drop event or other impact that could force the chassis 822 and the shell 820 into contact with one another.

Figure 8D:
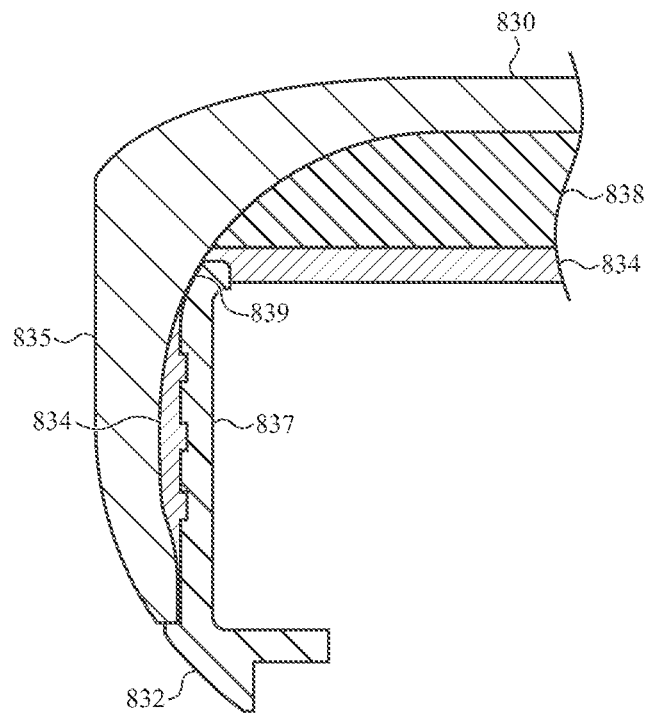

FIG. 8D illustrates another example configuration of a shell 830 and a chassis 832. In this example, the seal is omitted from at least a portion of the gap between the internal wall 837 and the side wall 835, such that adhesive 834 can flow out of the gap and into other areas of the device. For example, a channel 839 may be defined between the interior surface of the side wall 835 and the internal wall 837 of the chassis. When the adhesive 834 is introduced into the gap between the side wall 835 and the internal wall 837, the adhesive 834 may flow through the channel 839. As shown, the adhesive 834 flows along a rear-facing surface of a display stack 838. The adhesive 834 may act as a sealing or potting material to help seal and/or encapsulate the display stack 838 (which may include display components, touch-sensing and/or force-sensing components, or the like). The adhesive 834 may also act as a mask that inhibits visibility of internal components of the device.

The thickness of the adhesive 834 along the display stack 838 (or at any other locations outside of the gap between the side wall 835 and the internal wall 837) may be defined by placing a removable mold surface in the internal cavity defined by the shell 830 and the chassis 832. For example, a removable plate may be set apart from the rear-facing surface of the display stack 838. When the adhesive 834 is introduced into the gap between the side wall 835 and the internal wall 837, the adhesive 834 will flow into the gap, flow through the channel 839, and flow into the space between the removable plate and the display stack 838. Once at least partially cured and/or hardened, the removable plate may be removed. In cases where electrical components are covered and/or encapsulated by the adhesive 834, portions of the adhesive 834 may be ablated or removed to expose the components. For example, adhesive may be removed to expose electrical contacts, connectors, circuit elements, or other features or components. In some cases, the adhesive 834 may be prevented from contacting and/or covering the electrical connectors, contacts, circuit elements, or the like, so that they can be accessed without having to remove the adhesive 834 from those areas. While FIG. 8D illustrates the adhesive 834 covering at least part of the display stack 838, the adhesive 834 may be allowed to flow against other internal components as well. In some cases, the adhesive 834 may be injected so that it occupies substantially all of the otherwise unused or empty internal space in the device.

Figure 9A:
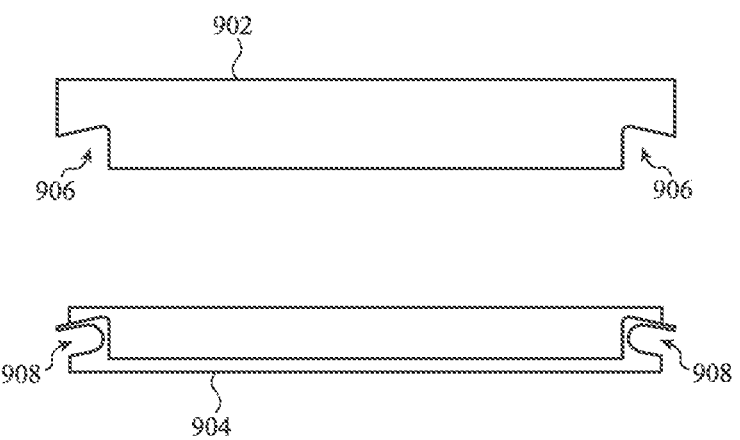
FIGS. 9A-9B depict an example housing for an electronic device.
Figure 9B:
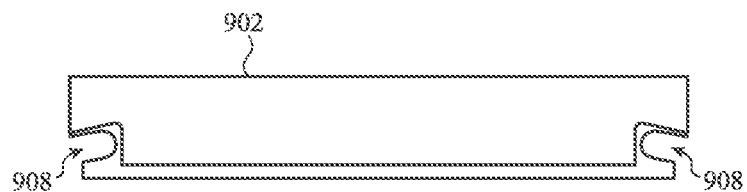

FIGS. 9A-9B illustrate an example shell 902 and chassis 904 that may be used to form at least part of a housing for a watch. The shell 902 and the chassis 904 may be embodiments of the shell 104 and the chassis 106, described above.

FIG. 9A shows the shell 902 separate from the chassis 904. As shown, the watch band engagement features 908 are defined entirely by the chassis 904. For example, all of the surfaces of the slots that are configured to receive the watch band are defined by the chassis 904. Also, the watch band engagement features 908 may be formed in the chassis 904 prior to the chassis 904 being attached to the shell 902. The shell 902 may define cutout regions 906 that engage with and/or accept a portion of the chassis 904 that forms the watch band engagement features 908. FIG. 9B is a side view of the shell 902 and the chassis 904 after being assembled. As shown in FIG. 9B, the shell 902 does not extend into or otherwise define any surfaces or edges of the watch band engagement features 908.

Figure 10A:
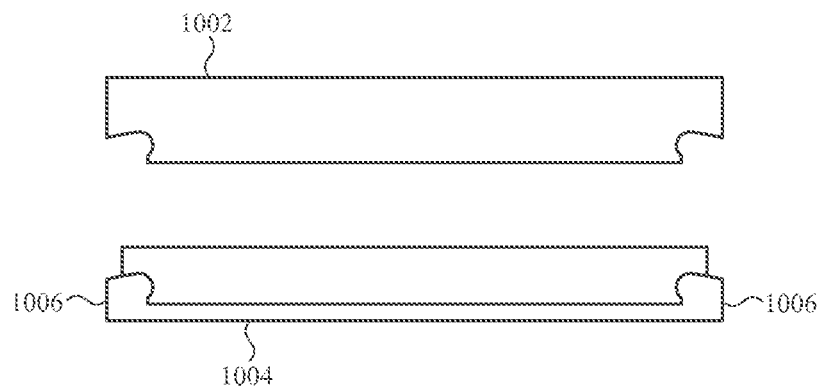
FIGS. 10A-10C depict another example housing for an electronic device.
Figure 10B:
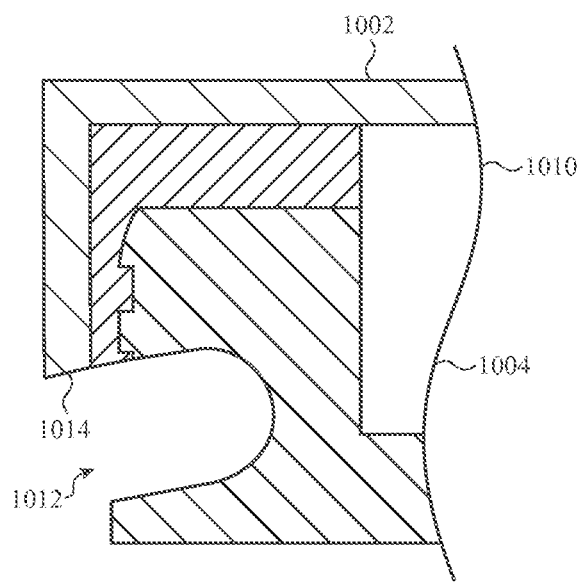
Figure 10C:
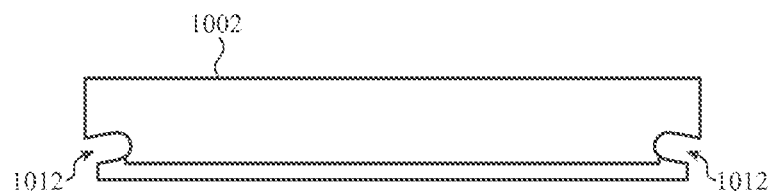

FIGS. 10A-10C illustrate an example shell 1002 and chassis 1004 that may be used to form at least part of a housing for a watch. More particularly, FIGS. 10A-10C illustrate an example configuration and manufacturing process in which watch band engagement features (e.g., slots) are formed after the shell 1002 and the chassis 1004 are assembled together, and in which a portion of the shell 1002 may define a portion of the watch band engagement features 1012.

FIG. 10A shows the shell 1002 separate from the chassis 1004. As shown, the chassis 1004 includes material at the locations 1006 where the watch band engagement features (e.g., watch band slots) are to be formed. Prior to forming the watch band engagement features, the shell 1002 may be attached to the chassis 1004. Adhesive (e.g., adhesive 1010, FIG. 10B) may be used to secure the shell 1002 to the chassis 1004. The adhesive 1010 may be applied using the techniques described with respect to FIGS. 7A-7B, for example.

Once the shell 1002 is secured to the chassis 1004, the assembly may be machined or otherwise processed to form the watch band engagement features 1012. FIG. 10C, for example, illustrates the shell 1002 and chassis 1004 after the watch band engagement features 1012 have been formed. The watch band engagement features 1012 may be formed by any suitable operation or operations, such as machining, grinding, laser or other beam-based cutting operation, or the like. Operations such as lapping and/or polishing may also be performed after a first material removal operation in order to produce a desired surface finish or texture (or lack of texture) on the surfaces of the watch band engagement features 1012.

In some cases, the operation of forming the watch band engagement features 1012 results in material being removed from both the shell 1002 and the chassis 1004. This may also result in the shell 1002 defining a portion of the watch band engagement features 1012. For example, as shown in FIG. 10B, an end surface 1014 of the shell 1002 may define part of a watch band slot, and a watch band, when attached to the housing via the watch band slot, may contact the end surface 1014 of the shell 1002. In some cases, a coating or covering may be applied to the end surface 1014 of the shell 1002. For example, a polymer coating may be applied to the end surface 1014 to prevent chipping or other damage to the shell 1002.

Figure 11:
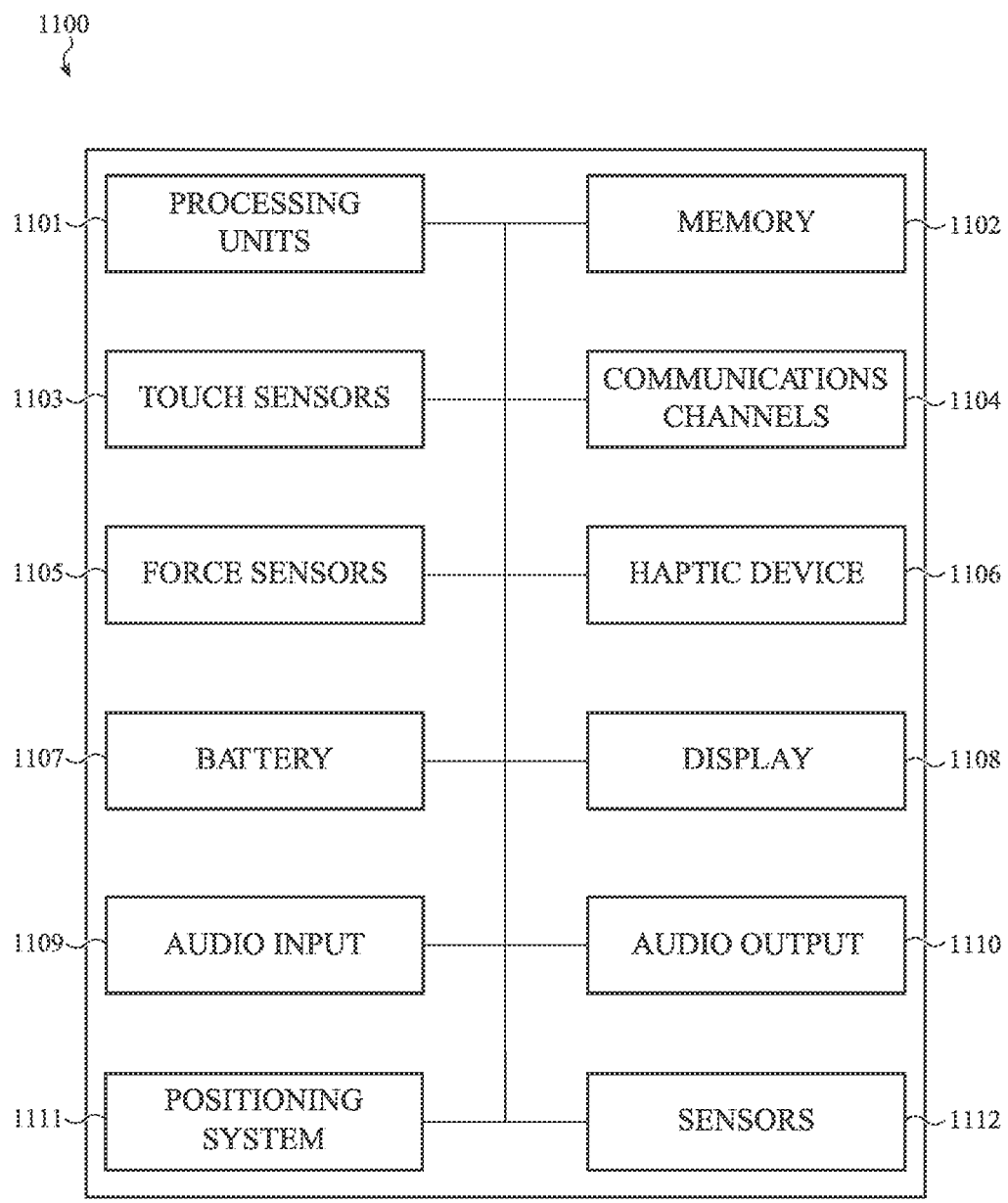
FIG. 11 depicts a schematic diagram of an example electronic device.

FIG. 11 depicts an example schematic diagram of an electronic device 1100. The electronic device 1100 may be an embodiment of or otherwise represent the watch 100 (or any other watches or device(s) described herein). The device 1100 includes one or more processing units 1101 that are configured to access a memory 1102 having instructions stored thereon. The instructions or computer programs may be configured to perform one or more of the operations or functions described with respect to the electronic devices described herein. For example, the instructions may be configured to control or coordinate the operation of one or more displays 1108, one or more touch sensors 1103, one or more force sensors 1105, one or more communication channels 1104, one or more audio input systems 1109, one or more audio output systems 1110, one or more positioning systems 1111, one or more sensors 1112, and/or one or more haptic feedback devices 1106.

The processing units 1101 of FIG. 11 may be implemented as any electronic device capable of processing, receiving, or transmitting data or instructions. For example, the processing units 1101 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements. The processing units 1101 may be coupled to a circuit board.

The memory 1102 can store electronic data that can be used by the device 1100. For example, a memory can store electrical data or content such as, for example, audio and video files, images, documents and applications, device settings and user preferences, programs, instructions, timing and control signals or data for the various modules, data structures or databases, and so on. The memory 1102 can be configured as any type of memory. By way of example only, the memory can be implemented as random access memory, read-only memory, Flash memory, removable memory, or other types of storage elements, or combinations of such devices.

The touch sensors 1103, also referred to herein as touch-sensing systems, may detect various types of touch-based inputs and generate signals or data that are able to be accessed using processor instructions. The touch sensors 1103 may use any suitable components and may rely on any suitable phenomena to detect physical inputs. For example, the touch sensors 1103 may be capacitive touch sensors, resistive touch sensors, acoustic wave sensors, or the like. The touch sensors 1103 may include any suitable components for detecting touch-based inputs and generating signals or data that are able to be accessed using processor instructions, including electrodes (e.g., electrode layers), physical components (e.g., substrates, spacing layers, structural supports, compressible elements, etc.) processors, circuitry, firmware, and the like. The touch sensors 1103 may be integrated with or otherwise configured to detect touch inputs applied to any portion of the device 1100. For example, the touch sensors 1103 may be configured to detect touch inputs applied to any portion of the device 1100 that includes a display (and may be integrated with a display). For example, the touch sensors 1103 may be configured to detect touch inputs applied to front and/or side surfaces of a shell. The touch sensors 1103 may operate in conjunction with the force sensors 1105 to generate signals or data in response to touch inputs. A touch sensor or force sensor that is positioned over a display or otherwise integrated with a display may be referred to herein as a touch-sensitive display, force-sensitive display, or touchscreen.

The force sensors 1105 may detect various types of force-based inputs and generate signals or data that are able to be accessed using processor instructions. The force sensors 1105 may use any suitable components and may rely on any suitable phenomena to detect physical inputs. For example, the force sensors 1105 may be strain-based sensors, piezoelectric-based sensors, piezoresistive-based sensors, capacitive sensors, resistive sensors, or the like. The force sensors 1105 may include any suitable components for detecting force-based inputs and generating signals or data that are able to be accessed using processor instructions, including electrodes (e.g., electrode layers), physical components (e.g., substrates, spacing layers, structural supports, compressible elements, etc.) processors, circuitry, firmware, and the like. The force sensors 1105 may be used in conjunction with various input mechanisms to detect various types of inputs. For example, the force sensors 1105 may be used to detect presses or other force inputs that satisfy a force threshold (which may represent a more forceful input than is typical for a standard "touch" input). Like the touch sensors 1103, the force sensors 1105 may be integrated with or otherwise configured to detect force inputs applied to any portion of the device 1100. As a specific example, force sensors 1105 may be configured to detect force inputs applied to the front and/or side surfaces of a shell. The force sensors 1105 may be configured to detect force inputs applied to portions of the device 1100 that include a display (and may be integrated with the display). The force sensors 1105 may operate in conjunction with the touch sensors 1103 to generate signals or data in response to touch- and/or force-based inputs.

The device 1100 may also include one or more haptic feedback devices 1106 (also referred to simply as haptic devices 1106). The haptic device 1106 may include one or more of a variety of haptic technologies such as, but not necessarily limited to, rotational haptic devices, linear actuators, piezoelectric devices, vibration elements, and so on. In general, the haptic device 1106 may be configured to provide punctuated and distinct feedback to a user of the device. More particularly, the haptic device 1106 may be adapted to produce a knock or tap sensation and/or a vibration sensation. Such haptic outputs may be provided in response to detection of touch and/or force inputs, and may be imparted to a user through an exterior surface of the device 1100 (e.g., via front, side, and/or rear surfaces of a wearable device such as a watch).

The one or more communication channels 1104 may include one or more wireless interface(s) that are adapted to provide communication between the processing unit(s) 1101 and an external device. The one or more communication channels 1104 may include antennas, communications circuitry, firmware, software, or any other components or systems that facilitate wireless communications with other devices. In general, the one or more communication channels 1104 may be configured to transmit and receive data and/or signals that may be interpreted by instructions executed on the processing units 1101. In some cases, the external device is part of an external communication network that is configured to exchange data with wireless devices. Generally, the wireless interface may communicate via, without limitation, radio frequency, optical, acoustic, and/or magnetic signals and may be configured to operate over a wireless interface or protocol. Example wireless interfaces include radio frequency cellular interfaces (e.g., 2G, 3G, 4G, 4G, 4G long-term evolution (LTE), 5G, GSM, CDMA, or the like), fiber optic interfaces, acoustic interfaces, Bluetooth interfaces, infrared interfaces, USB interfaces, Wi-Fi interfaces, TCP/IP interfaces, network communications interfaces, or any conventional communication interfaces.

As shown in FIG. 11, the device 1100 may include a battery 1107 that is used to store and provide power to the other components of the device 1100. The battery 1107 may be a rechargeable power supply that is configured to provide power to the device 1100. The battery 1107 may be coupled to charging systems (e.g., wired and/or wireless charging systems) and/or other circuitry to control the electrical power provided to the battery 1107 and to control the electrical power provided from the battery 1107 to the device 1100.

The device 1100 may also include one or more displays 1108 configured to display graphical outputs. The displays 1108 may use any suitable display technology, including liquid crystal displays (LCD), organic light emitting diodes (OLED), active-matrix organic light-emitting diode displays (AMOLED), or the like. The displays 1108 may display graphical user interfaces, images, icons, or any other suitable graphical outputs. The one or more displays 1108 may include displays that are configured to display graphical outputs that are visible through the front and/or side walls of a device. The one or more displays 1108 may correspond to the display 114, the display 402, or any other displays described herein.

The device 1100 may also provide audio input functionality via one or more audio input systems 1109. The audio input systems 1109 may include microphones, transducers, or other devices that capture sound for voice calls, video calls, audio recordings, video recordings, voice commands, and the like.

The device 1100 may also provide audio output functionality via one or more audio output systems (e.g., speakers) 1110. The audio output systems 1110 may produce sound from voice calls, video calls, streaming or local audio content, streaming or local video content, alerts or notifications, or the like.

The device 1100 may also include a positioning system 1111. The positioning system 1111 may be configured to determine the location of the device 1100. For example, the positioning system 1111 may include magnetometers, gyroscopes, accelerometers, optical sensors, cameras, global positioning system (GPS) receivers, inertial positioning systems, or the like. The positioning system 1111 may be used to determine spatial parameters of the device 1100, such as the location of the device 1100 (e.g., geographical coordinates of the device), measurements or estimates of physical movement of the device 1100, an orientation of the device 1100, or the like.

The device 1100 may also include one or more additional sensors 1112 to receive inputs (e.g., from a user or another computer, device, system, network, etc.) or to detect any suitable property or parameter of the device, the environment surrounding the device, people or things interacting with the device (or nearby the device), or the like. For example, a device may include temperature sensors, biometric sensors (e.g., fingerprint sensors, photoplethysmographs, blood-oxygen sensors, blood sugar sensors, electrocardiograph sensors, or the like), eye-tracking sensors, retinal scanners, humidity sensors, buttons, switches, or the like.

To the extent that multiple functionalities, operations, and structures described with reference to FIG. 11 are disclosed as being part of, incorporated into, or performed by the device 1100, it should be understood that various embodiments may omit any or all such described functionalities, operations, and structures. Thus, different embodiments of the device 1100 may have some, none, or all of the various capabilities, apparatuses, physical features, modes, and operating parameters discussed herein. Further, the systems included in the device 1100 are not exclusive, and the device 1100 may include alternative or additional systems, components, modules, programs, instructions, or the like, that may be necessary or useful to perform the functions described herein.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings. Also, when used herein to refer to positions of components, the terms above, below, over, under, left, or right (or other similar relative position terms), do not necessarily refer to an absolute position relative to an external reference, but instead refer to the relative position of components within the figure being referred to.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

What is claimed is:
1. A wearable electronic device comprising:
a display;
a housing comprising:
  a chassis defining:
    a rear portion defining a first portion of a rear exterior surface of the wearable electronic device; and
    an internal wall extending from the rear portion;
  a glass shell defining:
    a front wall positioned over the display and defining a front exterior surface of the wearable electronic device; and
    a side wall extending from the front wall and defining:
      a convex side exterior surface of the wearable electronic device; and
      a concave interior surface opposite the convex side exterior surface, a portion of the side wall overlapping a portion of the internal wall of the chassis such that a gap is defined between the concave interior surface of the side wall and the internal wall of the chassis; and an adhesive positioned in the gap defined between the concave interior surface of the side wall and the internal wall of the chassis, the adhesive bonded to the concave interior surface of the side wall and to the internal wall of the chassis; and a touch sensing system within the housing and configured to detect a touch input applied to the front exterior surface of the wearable electronic device.

2. The wearable electronic device of claim 1, wherein:
the adhesive defines an undercut region; and
the concave interior surface of the side wall mechanically interlocks with the undercut region of the adhesive to secure the glass shell to the chassis.

3. The wearable electronic device of claim 2, wherein the glass shell is secured to the chassis at least in part via a chemical bond between the concave interior surface and the adhesive.

4. The wearable electronic device of claim 1, further comprising a compliant member within the housing and in contact with the internal wall and the side wall, the compliant member defining a seal between the internal wall and the side wall and configured to retain the adhesive in the gap.

5. The wearable electronic device of claim 1, wherein the side wall extends more than half of a distance from the front exterior surface of the wearable electronic device to the rear exterior surface of the wearable electronic device.

6. The wearable electronic device of claim 1, wherein:
the front wall further defines a front interior surface of the wearable electronic device;
the wearable electronic device further comprises an opaque mask material on a portion of the concave interior surface and on a portion of the front interior surface; and
the opaque mask material defines a border around an active area of the display.

7. The wearable electronic device of claim 1, wherein the display defines:
a first portion configured to display first graphical outputs through the front wall; and
a second portion configured to display second graphical outputs through the side wall.

8. The wearable electronic device of claim 1, wherein the adhesive is formed by flowing a flowable material into the gap and allowing the flowable material to harden.

9. The wearable electronic device of claim 1, further comprising an opaque mask material between a portion of the concave interior surface and the adhesive and configured to visually occlude the adhesive.

10. A watch comprising:
a display;
a capacitive touch-sensing system; and
a housing surrounding the display and the capacitive touch-sensing system and comprising:
a chassis defining:
at least a portion of a rear surface of the watch;
a watch band engagement feature; and
an internal wall; and
a glass shell defining:
a front wall defining a front surface of the watch;
a first pair of side walls having a first length and defining a first pair of side surfaces of the watch; and
a second pair of side walls having a second length greater than the first length and defining a second pair of side surfaces of the watch, at least one side wall of the second pair of side walls defining a convex exterior surface and a concave interior surface opposite the convex exterior surface, a portion of the at least one side wall overlapping a portion of the internal wall such that a gap is defined between the concave interior surface and the internal wall;

an adhesive positioned in the gap defined between the concave interior surface and the internal wall, the adhesive bonded to the concave interior surface and to the internal wall; and a watch band coupled to the watch band engagement feature.

11. The watch of claim 10, wherein:
the chassis is formed from metal and defines:
a rear wall defining the portion of the rear surface of the watch; and
a hole extending through the rear wall; and
the watch further comprises:
a sensor cover positioned at least partially in the hole and defining an additional portion of the rear surface of the watch; and
a sensor system configured to detect a biological parameter of a user through the sensor cover.

12. The watch of claim 10, wherein the watch band engagement feature includes a slot formed in the chassis.

13. The watch of claim 10, wherein the display is configured to display graphical outputs visible through the front wall and through at least one side wall of the second pair of side walls.

14. The watch of claim 10, wherein:
the adhesive defines an undercut; and
the concave interior surface of the at least one side wall engages the undercut to mechanically interlock the glass shell to the chassis.

15. A wearable electronic device comprising:
a housing comprising:
a chassis defining:
a rear wall defining a first portion of a rear exterior surface of the wearable electronic device;
an internal wall extending from the rear wall; and
a hole extending through the rear wall;
a glass shell defining:
a front wall defining a front surface of the wearable electronic device; and
four side walls extending from the front wall, each of the four side walls defining a portion of a respective side surface of the wearable electronic device, at least one side wall of the four side walls defining a convex exterior surface and a concave interior surface opposite the convex exterior surface, a portion of the at least one side wall overlapping a portion of the internal wall such that a gap is defined between the concave interior surface and the internal wall; and
a sensor cover covering the hole and defining a second portion of the rear exterior surface of the wearable electronic device;
an adhesive positioned in the gap defined between the concave interior surface and the internal wall, the adhesive bonded to the concave interior surface and to the internal wall
a display within the housing; and
a biometric sensor system within the housing and configured to detect a biological parameter of a user.

16. The wearable electronic device of claim 15, wherein the biometric sensor system comprises:
an optical emitter configured to emit light through a first transparent portion of the sensor cover; and an optical sensor configured to detect, through a second transparent portion of the sensor cover, a portion of the light that is reflected by a portion of the user's body.

17. The wearable electronic device of claim 16, wherein the sensor cover comprises:
a monolithic structure formed from a transparent material;
a masked region defining an opaque region of the sensor cover;
a first unmasked region defining the first transparent portion of the sensor cover; and
a second unmasked region defining the second transparent portion of the sensor cover.

18. The wearable electronic device of claim 15, further comprising an electrode coupled to the sensor cover and defining a third portion of the rear exterior surface of the wearable electronic device.

19. The wearable electronic device of claim 18, wherein:
the electrode is a first electrode configured to measure a first voltage;
the wearable electronic device further comprises a second electrode along an exterior surface of the wearable electronic device and configured to measure a second voltage; and
the wearable electronic device is configured to determine an electrocardiogram using the first voltage and the second voltage.

20. The wearable electronic device of claim 19, wherein the second electrode is positioned along one of the side walls of the four side walls.

* * * * *